US006528509B1

(12) United States Patent
Hale et al.

(10) Patent No.: US 6,528,509 B1
(45) Date of Patent: Mar. 4, 2003

(54) PYRAZOLE COMPOSITIONS USEFUL AS INHIBITORS OF ERK

(75) Inventors: Michael Hale, Bedford, MA (US); Xiaoling Xie, Cambridge, MA (US); Jeremy Green, Burlington, MA (US); Jingrong Cao, Newton, MA (US); Christopher Baker, Bedford, MA (US); Francois Maltais, Somerville, MA (US); James Janetka, Beverly, MA (US); Guy Bemis, Arlington, MA (US); Michael Mullican, Needham, MA (US); Judith Straub, Cambridge, MA (US); Qing Tang, Cambridge, MA (US); Robert Mashal, West Newton, MA (US)

(73) Assignee: Vertex Pharmacuticals, Incorporated, Cambridge, MA (US)

( * ) Notice: Subject to any disclaimer, the term of this patent is extended or adjusted under 35 U.S.C. 154(b) by 0 days.

(21) Appl. No.: 09/972,437

(22) Filed: Oct. 5, 2001

Related U.S. Application Data
(60) Provisional application No. 60/242,935, filed on Oct. 24, 2000, provisional application No. 60/191,956, filed on Mar. 24, 2000, and provisional application No. 60/180,506, filed on Feb. 5, 2000.

(51) Int. Cl.[7] ............... A61K 31/5377; A61K 31/4155; A61P 35/00; C07D 403/04; C07D 413/10
(52) U.S. Cl. ............ 514/236.5; 540/575; 544/140; 544/295; 544/328; 544/367; 544/371; 544/363; 546/86; 546/146; 546/199; 546/273.7; 546/275.4; 546/211; 548/127; 548/312.4; 548/364.1; 548/364.4; 548/365.7
(58) Field of Search ............ 548/364.1, 364.4, 548/365.7; 544/140; 514/236.5

(56) References Cited

U.S. PATENT DOCUMENTS 5,922,741 A 7/1999 Davis et al. .............. 514/341

5,932,576 A 8/1999 Anantanarayan et al. 514/235.5

FOREIGN PATENT DOCUMENTS

| FR | 2 707 295 | 1/1995 |
|---|---|---|
| WO | WO 98/52941 | 11/1998 |

OTHER PUBLICATIONS

Ambiter company catalog, dated Aug. 23, 1999, discloses the compound "1H–pyrrole–2–carboxamide,N,N–dimethyl–4–(4–phenyl–1H–pyrazol–3–yl)". Copy not available to applicants.

Jones et al, "Pyrrole studies. Part XXIII. 1,3–Dipolar addition reactions with vinylpyrroles", Heterocycles, 14(2): 185–188, 1980 (see in particular p. 186, table I).

Zhestkov et al, "Synthesis and biological activity of pyrrole–substituted pyrazol–5–ones", Khim.–Farm. Zh., 16(6): 47–52, 1982 (see in particular p. 48, table I).

Primary Examiner—Robert W. Ramsuer
(74) Attorney, Agent, or Firm—Vertex Pharmaceuticals, Incorporated; Andrea L. C. Robidoux; Andrew B. Marks

(57) ABSTRACT

Described herein are compounds that are useful as protein kinase inhibitors having the formula:

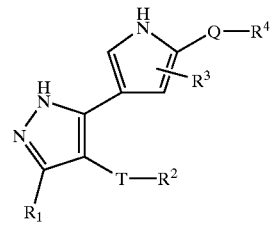

where $R^{1-4}$, Q, and T are described in the specification. The compounds are useful for treating disease states in mammals that are alleviated by a protein kinase inhibitor, particularly diseases such as cancer, inflammatory disorders, restenosis, and cardiovascular disease.

21 Claims, No Drawings

PYRAZOLE COMPOSITIONS USEFUL AS INHIBITORS OF ERK

This application claims the priority to co-pending International Patent Application PCT/US03911, filed Feb. 5, 2001, which claims priority of United States Provisional Application serial No. 60/180,506 filed Feb. 5, 2000; U.S. Provisional Application serial No. 60/242,935 filed Oct. 24, 2000; and U.S. Provisional Application serial No. 60/191,956 filed Mar. 24, 2000. The entire of which is herein incorporated by reference.

FIELD OF THE INVENTION

The present invention is in the field of medicinal chemistry and relates to pyrazole compounds that are protein kinase inhibitors, especially inhibitors of ERK, compositions containing such compounds and methods of use. The compounds are useful for treating cancer and other disease states that are alleviated by protein kinase inhibitors.

BACKGROUND OF THE INVENTION

Mammalian mitogen-activated protein (MAP)1 kinases are serine/threonine kinases that mediate intracellular signal transduction pathways (Cobb and Goldsmith, 1995, *J Biol. Chem.*, 270, 14843; Davis, 1995, *Mol. Reprod. Dev.* 42, 459). Members of the MAP kinase family share sequence similarity and conserved structural domains, and include the ERK (extracellular signal regulated kinase), JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995, *J Biol. Chem.* 270, 7420; Shapiro and Dinarello, 1995, *Proc. Natl. Acad. Sci. USA* 92, 12230). In contrast, ERKs are activated by mitogens and growth factors (Bokemeyer et al. 1996, *Kidney Int.* 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; Crews et al., 1992, *Science* 258, 478). Upon activation, ERK2 phosphorylates many regulatory proteins, including the protein kinases Rsk90 (Bjorbaek et al., 1995, *J. Biol. Chem.* 270, 18848) and MAPKAP2 (Rouse et al., 1994, *Cell* 78, 1027), and transcription factors such as ATF2 (Raingeaud et al., 1996, *Mol. Cell Biol.* 16, 1247), Elk-1 (Raingeaud et al. 1996), c-Fos (Chen et al., 1993 *Proc. Natl. Acad. Sci. USA* 90, 10952), and c-Myc (Oliver et al., 1995, *Proc. Soc. Exp. Biol. Med.* 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J Clin. Invest.* 99, 1478). Activated ERK2 has also been implicated in the proliferation of endothelin-stimulated airway smooth muscle cells, suggesting a role for this kinase in asthma (Whelchel et al., 1997, *Am. J. Respir. Cell Mol. Biol.* 16, 589).

The JNK family of (MAP)1 kinases have been implicated in having a role in mediating cellular response to a variety of disorders including cancer (*Oncogene* 1996, 13, 135–42), hepatic disorders (*Hepatology* 1998, 28,1022–30), cardiovascular disease (*Circ. Res.* 1998, 83, 167–78; *Circulation* 1998, 97:1731–7; *J. Biol. Chem.* 1997, 272, 28050–6; *Circ. Res.* 1996, 79, 162–73; *Circ. Res.* 1996, 78, 947–53; *J. Clin. Invest.* 1996, 97, 508–14), and immunological disorders (*J. Immunol.* 1999, 162, 3176–87; *Eur. J. Immunol.* 1998, 28, 3867–77; *J. Exp. Med.* 1997, 186, 941–53; *Eur. J. Immunol.* 1996, 26, 989–94, among others).

Aurora2 is a serine/threonine protein kinase that has been implicated in human cancer, such as colon, breast and other solid tumors. This kinase is believed to be involved in protein phosphorylation events that regulate the cell cycle. Specifically, aurora2 may play a role in controlling the accurate segregation of chromosomes during mitosis. Misregulation of the cell cycle can lead to cellular proliferation and other abnormalities. In human colon cancer tissue, the aurora2 protein has been found to be overexpressed. See Bischoff et al., *EMBO J.*, 1998, 17, 3052–3065; Schumacher et al., *J. Cell Biol.*, 1998, 143, 1635–1646; Kimura et al., *J. Biol. Chem.*, 1997, 272, 13766–13771.

Glycogen synthase kinase-3 (GSK-3) is a serine/threonine protein kinase comprised of α and β isoforms that are each encoded by distinct genes [Coghlan et al., *Chemistry & Biology*, 7, 793–803 (2000); Kimand Kimmel, *Curr. Opinion Genetics Dev.*, 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role.

KDR is a tyrosine kinase receptor that also binds VEGF (vascular endothelial growth factor) (Neufeld et al., 1999, *FASEB J.*, 13, 9). The binding of VEGF to the KDR receptor leads to angiogenesis, which is the sprouting of capillaries from preexisting blood vessels. High levels of VEGF are found in various cancers causing tumor angiogenesis and permitting the rapid growth of cancerous cells. Therefore, suppressing VEGF activity is a way to inhibit tumor growth, and it has been shown that this can be achieved by inhibiting KDR receptor tyrosine kinase.

AKT, also known as protein kinase B, is a serine/threonine kinase that plays a central role in promoting the survival of a wide range of cell types [Khwaja, A., *Nature*, pp. 33–34 (1990)]. It has been shown by Zang, et al, that human ovarian cancer cells display elevated levels of AKT-1 and AKT-2. Inhibition of AKT induces apoptosis of these human ovarian cancer cells which demonstrates that AKT may be an important target for ovarian cancer treatment [Zang, Q. Y., et al, *Oncogene*, 19 (2000)] and other proliferative disorders. The AKT pathway has also been implicated in motoneuronal survival and nerve regeneration [Kazuhiko, N., et al, *The Journal of Neuroscience*, 20 (2000)].

There is a high unmet medical need to develop protein kinase inhibitors, especially ERK inhibitors, that are useful in treating the various conditions associated with ERK activation, especially considering the currently available, relatively inadequate treatment options for the majority of these conditions.

Accordingly, there is still a great need to develop potent inhibitors of protein kinase, including ERK inhibitors, that are useful in treating various conditions associated with protein kinase activation.

DESCRIPTION OF THE INVENTION

It has now been found that compounds of this invention and compositions thereof are effective as protein kinase inhibitors, especially as inhibitors of ERK. These compounds have the general formula I:

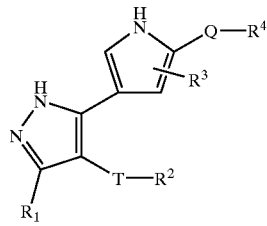

or a pharmaceutically acceptable derivative thereof, wherein:

$R^1$ is selected from R, halogen, $N(R^8)_2$, OR, NRCOR, $NRCON(R^8)_2$, $CON(R^8)_2$, $SO_2R$, $NRSO_2R$, or $SO_2N(R^8)_2$;

T is selected from a valence bond or a linker group;

each R is independently selected from hydrogen or an optionally substituted aliphatic group having one to six carbons;

$R^2$ is selected from hydrogen, CN, halogen, aryl, aralkyl, heteroaryl, heterocyclyl, an optionally substituted acyclic aliphatic chain group having one to six carbons, or an optionally substituted cyclic aliphatic group having four to ten carbons;

$R^3$ is selected from R, OH, OR, $N(R^8)_2$, halogen, or CN;

Q is a valence bond, J, or an optionally substituted $C_{1-6}$ alkylidene chain wherein up to two nonadjacent carbons of the alkylidene chain are each optionally and independently replaced by J;

J is selected from —C(=O)—, —CO$_2$—, —C(O)C(O)—, —NRCONR$^8$—, —N(R)N(R$^8$)—, —C(=O)NR$^8$—, —NRC(=O)—, —O—, —S—, —SO—, —SO$_2$—, —N(R)O—, —ON(R$^8$)—, —OC(=O)N(R$^8$)—, —N(R)COO—, —SO$_2$N(R$^8$)—, —N(R)SO$_2$—, or —N(R$^8$)—;

$R^4$ is selected from —R$^8$, —R$^5$, —NH$_2$, —NHR$^5$, —N(R$^5$)$_2$, or —NR$^5$(CH$_2$)$_y$N (R$^5$)$_2$;

each $R^5$ is independently selected from $R^6$, $R^7$, —(CH$_2$)$_y$CH(R$^6$)(R$^7$), —(CH$_2$)$_y$R$^6$, —(CH$_2$)$_y$CH(R$^6$)$_2$, —(CH$_2$)$_y$CH(R$^7$)$_2$, or —(CH$_2$)$_y$R$^7$;

y is 0–6;

each $R^6$ is an optionally substituted group independently selected from an aliphatic, aryl, aralkyl, aralkoxy, heteroaryl, heteroarylalkyl, heteroarylalkoxy, heterocyclyl, heterocyclylalkyl, or heterocyclylalkoxy, group;

each $R^7$ is independently selected from an optionally substituted hydroxyalkyl, alkoxyalkyl, aryloxyalkyl, or alkoxycarbonyl; and each $R^8$ is independently selected from R, or two $R^8$ on the same nitrogen taken together with the nitrogen optionally form a four to eight membered, saturated or unsaturated heterocyclic ring having one to three heteroatoms.

As used herein, the following definitions shall apply unless otherwise indicated. Also, combinations of substituents or variables are permissible only if such combinations result in stable compounds.

The term "aliphatic" as used herein means straight chained, branched or cyclic $C_1$–$C_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl) alkenyl. The term "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms. The terms "haloalkyl", "haloalkenyl" and "haloalkoxy" means alkyl, alkenyl or alkoxy, as the case may be, substituted with one or more halogen atoms. The term "halogen" means F, Cl, Br, or I. The term "heteroatom" means N, O, or S and shall include any oxidized form of nitrogen and sulfur, and the quaternized form of any basic nitrogen.

The term "aryl", used alone or as part of a larger moiety as in "aralkyl", refers to aromatic ring groups having five to fourteen members, such as phenyl, benzyl, 1-naphthyl, 2-naphthyl, 1-anthracyl and 2-anthracyl, and heterocyclic aromatic groups or heteroaryl groups such as 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, or 3-thienyl. The term "aryl ring" also refers to rings that are optionally substituted.

Aryl groups also include fused polycyclic aromatic ring systems in which a carbocyclic aromatic ring or heteroaryl ring is fused to one or more other rings. Examples include tetrahydronaphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, and the like. Also included within the scope of the term "aryl", as it is used herein, is a group in which one or more carbocyclic aromatic rings and/or heteroaryl rings are fused to a cycloalkyl or non-aromatic heterocyclic ring, for example, indanyl or tetrahydrobenzopyranyl.

Non-aromatic heterocyclic rings are non-aromatic carbocyclic rings in which one or more ring carbons are replaced by a heteroatom such as nitrogen, oxygen or sulfur in the ring. The ring can be five, six, seven or eight-membered and/or fused to another ring, such as a cycloalkyl or aromatic ring. Examples include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, and benzothiane. The term "heterocyclic ring", whether saturated or unsaturated, also refers to rings that are optionally substituted.

An aryl group (carbocyclic and heterocyclic) or an aralkyl group, such as benzyl or phenethyl, may contain one or more substituents. Examples of suitable substituents on the unsaturated carbon atom of an aryl group include a halogen, —R, —OR, —SR, protected OH (such as acyloxy), phenyl (Ph), substituted Ph, —OPh, substituted —OPh, —NO$_2$, —CN, —N(R)$_2$, —NRN(R)$_2$, —NRCON(R)$_2$, —NRCOR, —NRCO$_2$(aliphatic), —CO$_2$R, —COR, —C(O)C(O)R, —CON(R)$_2$, —CONRN(R)$_2$, —S(O)$_2$R, —SON(R)$_2$, —S(O) (aliphatic), —SO$_2$N(R)$_2$, or —NRS(O)$_2$R, where each R is independently selected from hydrogen, an aliphatic group or a substituted aliphatic group.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon as well as the following: =O, =S, =NNHR, =NNR$_2$, =N—, OR, =NNHCOR, =NNHCO$_2$ (aliphatic), =NNHSO$_2$ (aliphatic), or =NR, where each R is independently selected from hydrogen, an aliphatic group or a substituted aliphatic group.

The term "alkylidene chain" refers to an optionally substituted, straight or branched, carbon chain that may be fully saturated or have one or more units of unsaturation. The optional substituents are as described above for an aliphatic group. Optional substituents of the C$_{1-6}$ alkylidine chain of Q include those described above for an aliphatic group.

The term "linker group" means an organic moiety that connects two parts of a compound. Linkers are typically comprised of an atom such as oxygen or sulfur, a unit such as —NH— or —CH$_2$—, or a chain of atoms, such as an alkylidene chain. The molecular mass of a linker is typically in the range of about 14 to 200. Examples of linkers include a saturated or unsaturated C$_{1-6}$ alkylidene chain which is optionally substituted, and wherein up to two saturated carbons of the chain are optionally replaced by —C(=O)—, —CONH—, CONHNH—, —CO$_2$—, —NHCO$_2$—, —O—, —NHCONH—, —OC(=O)—, —OC(=O)NH—, —NHNH—, —NHCO—, —O—, —S—, —SO—, —SO$_2$—, —NH—, —SO$_2$NH—, or NHSO$_2$—.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

One embodiment of this invention relates to compounds of formula II:

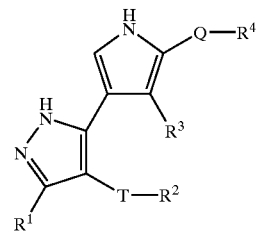

II wherein R$^1$, R$^2$, R$^3$, R$^4$, T, and Q are as described above.

A preferred embodiment of this invention relates to compounds having the formula:

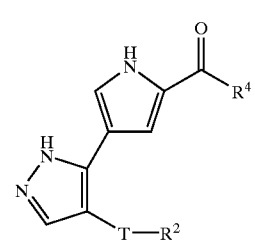

II-A wherein T, R$^2$, and R$^4$ are as described above and R$^1$ and R$^3$ are each hydrogen.

Preferred compounds include those having one or more, and most preferably all, of the following features: (a) Q is —CO—, —CO$_2$—, or —CONH—; (b) T is a valence bond; (c) R$^1$ is hydrogen or NHR; (d) R$^2$ is an optionally substituted aryl ring, more preferably an optionally substituted phenyl ring; (e) R$^3$ is hydrogen; (e) R$^4$ is selected from R$^5$, —NHR$^5$, —N(R$^5$)$_2$, —NR$^5$R$^6$, —NHCHR$^5$R$^6$, or —NHCH$_2$R$^5$; and/or (f) R$^5$ is an optionally substituted group selected from aryl, aralkyl, heteroaryl, heteroarylalkyl, heterocyclyl, heterocyclylalkyl group, (CH$_2$)$_y$R$^6$, (CH$_2$)$_y$R$^7$ or (CH$_2$)$_y$CH(R$^6$)(R$^7$).

Examples of substitutions of the R$^2$ phenyl group include halo, nitro, alkoxy, and amino.

When R$^4$ is R$^5$, examples of preferred R$^5$ groups include pyrrolidin-1-yl, morpholin-1-yl, piperidin-1-yl, and piperazin-1-yl wherein each group is optionally substituted. When R$^4$ is —NHR$^5$ or —N(R$^5$)$_2$, preferred R$^5$ groups further include (CH$_2$)$_y$R$^6$, (CH$_2$)$_y$R$^7$, and (CH$_2$)$_y$CH(R$^6$) (R$^7$). Examples of preferred R$^6$ and R$^7$ include pyridin-3-yl, pyridin-4-yl, imidazolyl, furan-2-yl, tetrahydrofuran-2-yl, cyclohexyl, phenyl, —CH$_2$OH, —(CH$_2$)$_2$OH, and isopropyl, wherein each group is optionally substituted.

Exemplary structures of formula II, wherein R$^1$ and R$^3$ are each H, are set forth in Table 1 below.

TABLE 1

Compounds II

| No. | T—R² | Q—R⁴ |
|---|---|---|
| II-1 | phenyl | CON(Me)$_2$ |
| II-2 | phenyl | CO$_2$Et |
| II-3 | 3-NO$_2$-phenyl | CONHNH$_2$ |
| II-4 | phenyl | CO(pyrrolidin-1-yl) |
| II-5 | phenyl | CONHCH$_2$(Ph) |
| II-6 | 3-NO$_2$-phenyl | CO$_2$Et |
| II-7 | 4-Cl-phenyl | CO$_2$Et |
| II-8 | 4-OMe-phenyl | CO$_2$Et |
| II-9 | 3-NH$_2$-phenyl | CO$_2$Et |
| II-10 | 3-OMe-phenyl | CO$_2$Et |
| II-11 | 4-F-phenyl | CO$_2$Et |
| II-12 | 4-NO$_2$-phenyl | CO$_2$Et |
| II-13 | 3-Cl-phenyl | CO$_2$Et |
| II-14 | 3-F-phenyl | CO$_2$Et |
| II-15 | phenyl | CO$_2$H |
| II-16 | 4-NH$_2$-phenyl | CO$_2$Et |
| II-17 | phenyl | CONHCH$_2$CH$_2$N(Me)$_2$ |
| II-18 | phenyl | CONHCH$_2$(pyridin-3-yl) |
| II-19 | phenyl | CO(morpholin-1-yl) |
| II-20 | phenyl | CONH(isopropyl) |
| II-21 | phenyl | CO(4-Me-piperazin-1-yl) |
| II-22 | phenyl | CONHCH$_2$(furan-2-yl) |
| II-23 | 3-OMe-phenyl | CONMe$_2$ |
| II-24 | 3-OMe-phenyl | CO(pyrrolidin-1-yl) |
| II-25 | 3-OMe-phenyl | CONHCH$_2$CH$_2$N(Me)$_2$ |
| II-26 | 3-OMe-phenyl | CONHCH$_2$(pyridin-3-yl) |
| II-27 | 3-OMe-phenyl | CO(morpholin-1-yl) |
| II-28 | 3-OMe-phenyl | CONH(isopropyl) |
| II-29 | 3-OMe-phenyl | CO(4-Me-piperazin-1-yl) |
| II-30 | 3-OMe-phenyl | CONHCH$_2$(furan-2-yl) |
| II-31 | 4-NH$_2$-phenyl | CO$_2$Et |
| II-32 | H | CONMe$_2$ |
| II-33 | H | CO(pyrrolidin-1-yl) |
| II-34 | 3-(AcNH)-phenyl | CO$_2$Et |
| II-35 | 4-(AcNH)-phenyl | CO$_2$Et |
| II-36 | 3-(AcNH)-phenyl | CO$_2$Et |
| II-37 | 4-(AcNH)-phenyl | CO$_2$Et |
| II-38 | 3-Cl-phenyl | CON(H)Bn |
| II-39 | 3,5-Cl$_2$-phenyl | C(=O)NH-CH(Ph)(CH$_2$OH) |
| II-40 | 5-Br-phenyl | CONH(3,4-F$_2$-phenyl) |
| II-41 | 5-Cl-phenyl | CONH(2-OH-1-Ph-ethyl) |
| II-42 | 4-OH,3-I,5-nitrophenyl | CONH(2-OH-1-Ph-ethyl) |
| II-43 | 5-Br-phenyl | C(=O)NH-CH$_2$-(2,3-dihydrobenzofuran-5-yl) |
| II-44 | 3-NH$_2$,4-OH,5-I-phenyl | CONH(2-OH-1-Ph-ethyl) |
| II-45 | 5-Br-phenyl | CONH(2-OH-1-Ph-ethyl) |
| II-46 | 5-Br-phenyl | CONHCH$_2$(3-MeO-phenyl) |

TABLE 1-continued

Compounds II

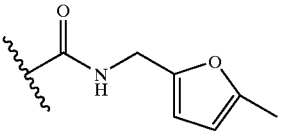

| No. | T—R² | Q—R⁴ |
|---|---|---|
| II-47 | 5-Br-phenyl | CONHCH₂(3-CF₃-phenyl) |
| II-48 | 3,5-Cl₂-phenyl | CONHCH₂(pyrid-4-yl) |
| II-49 | 5-CF₃-phenyl | CONH(2-OH-1-Ph-ethyl) |
| II-50 | 5-Cl-phenyl | CONHCH₂Ph |
| II-51 | 3,5-Cl₂-phenyl | CONHOCH₂Ph |
| II-52 | 4-OH,3-I,5-nitrophenyl | CONHCH₂Ph |
| II-53 | 5-Cl-phenyl | CONHCH₂(pyrid-4-yl) |
| II-54 | 4,5-Cl₂-phenyl | CONHOCH₂Ph |
| II-55 | 5-Br-phenyl | CONHCH₂(4-SO₂Me-phenyl) |
| II-56 | 5-Br-phenyl | CONHNH(3-CF₃-phenyl) |
| II-57 | 5-Cl-phenyl | CONHOCH₂Ph |
| II-58 | 5-Br-phenyl | 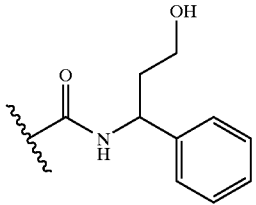 |
| II-59 | 5-Br-phenyl | 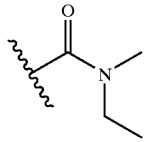 |
| II-60 | 5-Br-phenyl | CONHCH₂(2-Me-phenyl) |
| II-61 | 4,5-Cl₂-phenyl | CONHCH₂(pyrid-4-yl) |
| II-62 | 5-Br-phenyl | CONH(1-Ph-propyl) |
| II-63 | 5-F-phenyl | CONHCH₂Ph |
| II-64 | 4,5-Cl₂-phenyl | 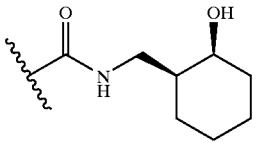 |
| II-65 | 5-Br-phenyl | |
| II-66 | 3,5-Cl₂-phenyl | CON(Me)(Et) |
| II-67 | 5-Cl-phenyl | CONHCH₂(pyrid-3-yl) |
| II-68 | 5-Br-phenyl | CONHCH₂(3,5-OMe₂-phenyl) |
| II-69 | 5-Br-phenyl | CONHCH₂(2-OMe-phenyl) |
| II-70 | 4-F-5-Cl-phenyl | CONHCH₂(pyrid-4-yl) |
| II-71 | 4-F-5-Cl-phenyl | CON(Me)(Et) |
| II-72 | 5-Br-phenyl | CONH(2-OH-1-Ph-ethyl) |
| II-73 | 5-NH₂-phenyl | CONHCH₂Ph |
| II-74 | 4,5-Cl₂-phenyl | CONHCH₂(pyrid-3-yl) |
| II-75 | 5-Me-phenyl | CONH(2-OH-1-Ph-ethyl) |
| II-76 | 3,5-Cl₂-phenyl | CONHCH₂(pyrid-3-yl) |
| II-77 | 4-F-5-Cl-phenyl | CONHOCH₂Ph |

TABLE 1-continued

Compounds II

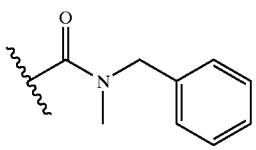

| No. | T—R² | Q—R⁴ |
|---|---|---|
| II-78 | 3,5-Cl₂-phenyl | CONHCH₂(tetrahydrofuran-2-yl) |
| II-79 | 5-NO₂-phenyl | CONHCH₂Ph |
| II-80 | 5-F-phenyl | CONHCH₂(pyrid-4-yl) |
| II-81 | 5-Cl-6-F-phenyl | CON(Me)(Et) |
| II-82 | 2-F-3-Cl-phenyl | CONHOCH₂Ph |
| II-83 | 5-Br-phenyl | 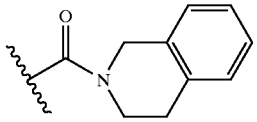 |
| II-84 | 5-Cl-phenyl | CONHCH₂(tetrahydrofuran-2-yl) |
| II-85 | 4,5-F₂-phenyl | CONHOCH₂Ph |
| II-86 | 5-Br-phenyl | CONH(3-OH-1-Ph-propyl) |
| II-87 | 5-Br-phenyl | 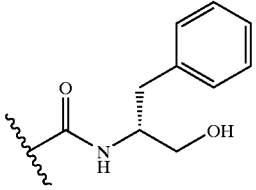 |
| II-88 | 4,5-F₂-phenyl | CONHCH₂(pyrid-4-yl) |
| II-89 | 5-F-phenyl | CONHOCH₂Ph |
| II-90 | 5-Me-phenyl | CONHCH₂Ph |
| II-91 | 5-Br-phenyl | 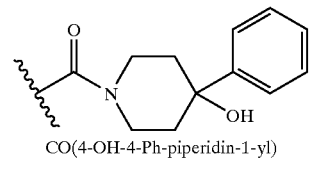 |
| II-92 | 4-Cl-phenyl | CONHCH₂Ph |
| II-93 | 5-Cl-phenyl | CON(Me)(Et) |
| II-94 | 5-Br-phenyl | CONHCH₂(4-SO₂NH₂-phenyl) |
| II-95 | 5-OH-phenyl | CONHCH₂Ph |
| II-96 | 5-Me-phenyl | CONHCH₂(pyrid-4-yl) |
| II-97 | Phenyl | CONHCH₂Ph |
| II-98 | 2,5-F₂-phenyl | CONHCH₂(pyrid-4-yl) |
| II-99 | 4-Cl-phenyl | CONHOCH₂Ph |
| II-100 | 4-F-5-Cl-phenyl | CONHCH₂(tetrahydrofuran-2-yl) |
| II-101 | 4-F-5-Cl-phenyl | CONHCH₂(pyrid-3-yl) |
| II-102 | 5-Br-phenyl | CO(4-OH-4-Ph-piperidin-1-yl) |
| II-103 | 5,6-F₂-phenyl | CONHOCH₂Ph |
| II-104 | 5-Cl-phenyl | CO(morpholin-1-yl) |

TABLE 1-continued

Compounds II

| No. | T—R² | Q—R⁴ |
|---|---|---|
| II-105 | 5-Br-phenyl | (structure: acyl-tetrahydroisoquinoline with CH₂OH, 6,7-dimethoxy) |
| II-106 | 2-F-3-Cl-phenyl | CONHCH₂(tetrahydrofuran-2-yl) |
| II-107 | 4-F-5-Cl-phenyl | CO(morpholin-1-yl) |
| II-108 | 4-F-5-Cl-phenyl | CON(Me)(Et) |
| II-109 | 5-Br-phenyl | CONHCH₂(4-NH₂-phenyl) |
| II-110 | 5-Br-phenyl | (structure: CONHCH₂-(4-(1,2,3-thiadiazol-5-yl)phenyl)) |
| II-111 | 4-F-phenyl | CONHCH₂Ph |
| II-112 | 3,5-Cl₂-phenyl | CO(morpholin-1-yl) |
| II-113 | 2,5-F₂-phenyl | CONHOCH₂Ph |
| II-114 | 2-F-3-Cl-phenyl | CONHCH₂(pyrid-3-yl) |
| II-115 | 2-F-3-Cl-phenyl | CONHCH₂(pyrid-4-yl) |
| II-116 | 4,5-F₂-phenyl | CONHCH₂(pyrid-3-yl) |
| II-117 | 4-OMe-phenyl | CONHCH₂Ph |
| II-118 | 5-Br-phenyl | CONHCH₂(2,4,6-OMe₃-phenyl) |
| II-119 | 5-F-phenyl | CONHCH₂(pyrid-3-yl) |
| II-120 | 4,5-F₂-phenyl | CONHCH₂(tetrahydrofuran-2-yl) |
| II-121 | 5-Cl-6-F-phenyl | (structure: CONHCH₂-(N-Boc-piperidin-3-yl)) |
| II-122 | 5-Br-phenyl | (structure: acyl-piperazine-N-(3-methoxyphenyl)) |
| II-123 | 5-Br-phenyl | (structure: acyl-4-(4-bromophenyl)-4-hydroxypiperidine) |
| II-124 | 5-Br-phenyl | CONHCH₂(2,5-OMe₂-phenyl) |

TABLE 1-continued

Compounds II

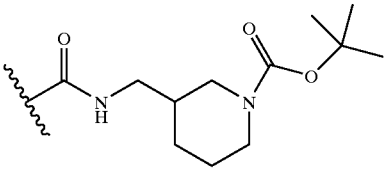

| No. | T—R² | Q—R⁴ |
|---|---|---|
| II-125 | 3,5-Cl₂-phenyl | 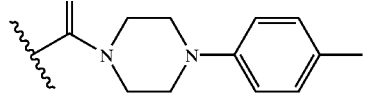 |
| II-126 | 5-Br-phenyl | 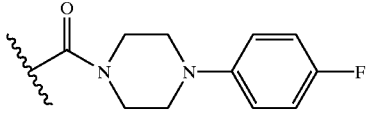 |
| II-127 | 4,5-Cl₂-phenyl | CO(morpholin-1-yl) |
| II-128 | 5-Br-phenyl | 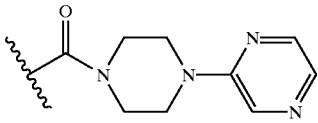 |
| II-129 | 2-F-3-Cl-phenyl | CO(morpholin-1-yl) |
| II-130 | 5-Br-phenyl | CONHCH₂CH₂OH |
| II-131 | 5-NH₂-phenyl | CONHCH₂Ph |
| II-132 | 5-MeOC(O)-phenyl | CONHCH₂Ph |
| II-133 | 4-MeO-phenyl | CONHOCH₂Ph |
| II-134 | phenyl | CO(pyrrolidin-1-yl) |
| II-135 | 5-MeO-phenyl | CO(morpholin-1-yl) |
| II-136 | 5-Cl-phenyl | CO(4-Me-piperidin-1-yl) |
| II-137 | 5-NO₂-phenyl | CONH₂NH₂ |
| II-138 | 5-Br-phenyl | 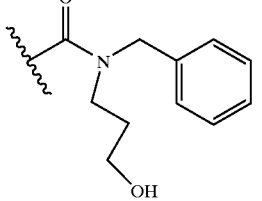 |
| II-139 | 5-Br-phenyl | 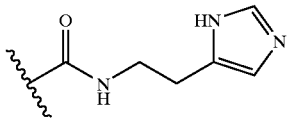 |
| II-140 | 5-Cl-phenyl | CONHPh |
| II-141 | 5,6-F₂-phenyl | CONHCH₂(pyrid-4-yl) |
| II-142 | 5-Cl-phenyl |  |
| II-143 | phenyl | CON(Me)₂ |

TABLE 1-continued

Compounds II

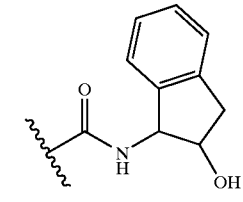

| No. | T—R² | Q—R⁴ |
|---|---|---|
| II-144 | 5-OMe-phenyl | Co(pyrrolidin-1-yl) |
| II-145 | 5-OMe-phenyl | CONHCH₂(pyrid-3-yl) |
| II-146 | 4-F-phenyl | CONHOCH₂Ph |
| II-147 | 5-OMe-phenyl | CONHCH₂(furan-2-yl) |
| II-148 | 5-NO₂-phenyl | COOEt |
| II-149 | phenyl | CONHCH₂(furan-2-yl) |
| II-150 | phenyl | CO(morpholin-1-yl) |
| II-151 | 5-Cl-phenyl | COOEt |
| II-152 | 5-Br-phenyl | CONHMe |
| II-153 | phenyl | CONHCH₂(pyrid-3-yl) |
| II-154 | 5-OMe-phenyl | CON(Me)₂ |
| II-155 | 5-Cl-phenyl | 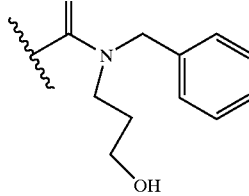 |
| II-156 | 5#Br-phenyl | 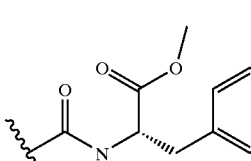 |
| II-157 | 5-Br-phenyl | COOEt |
| II-158 | phenyl | CONH(iPr) |
| II-159 | 5-OMe-phenyl | CONH(iPr) |
| II-160 | 5-COOH-phenyl | CONH(iPr) |
| II-161 | 5-Br-phenyl | CONHO(iPr) |
| II-162 | 5-F-phenyl | COOEt |
| II-163 | 5-OMe-phenyl | CO(4-Me-piperidin-1-yl) |
| II-164 | 4-NH₂-phenyl | COOEt |
| II-165 | 4-NO₂-phenyl | COOEt |
| II-166 | pheny | CO(4-Me-piperidin-1-yl) |
| II-167 | 4-Cl-phenyl | COOEt |
| II-168 | 4-OMe-phenyl | COOEt |
| II-169 | pheny | COOEt |
| II-170 | 5-OMe-phenyl | COOEt |
| II-171 | 4-F-phenyl | COOEt |
| II-172 | 5-NH₂-phenyl | COOEt |
| II-173 | 5-Cl-pheny1 | COOH |
| II-174 | 5-Cl-phenyl | |

Note: II-174 Q—R⁴ structure shown as methyl ester of phenylalanine amide.

TABLE 1-continued

Compounds II

| No. | T—R² | Q—R⁴ |
|---|---|---|
| II-175 | 5-Cl-phenyl | tert-butyl 2-phenyl-2-(acylamino)acetate group |
| II-176 | 5-OMe-phenyl | CONHCH₂(pyrid-4-yl) |
| II-177 | 3,5-(OMe)₂-phenyl | CONHCH₂(pyrid-4-yl) |
| II-178 | 4-F-phenyl | CONHCH₂(pyrid-3-yl) |
| II-179 | 4-OMe-phenyl | CONHCH₂(pyrid-3-yl) |
| II-180 | 2,5-(OM3)₂-phenyl | CONHCH₂(pyrid-3-yl) |
| II-181 | 2,5-F₂-phenyl | CONHCH₂(pyrid-3-yl) |
| II-182 | 4-F-phenyl | CONHCH₂(tetrahydrofuran-2-yl) |
| II-183 | 4-OMe-phenyl | CONHCH₂(tetrahydrofuran-2-yl) |
| II-184 | 5-F-phenyl | CONHCH₂(tetrahydrofuran-2-yl) |
| II-185 | 5-OMe-phenyl | CONHCH₂(tetrahydrofuran-2-yl) |
| II-186 | 2,5-(OMe)₂-phenyl | CONHCH₂(tetrahydrofuran-2-yl) |
| II-187 | 5,6-F₂-phenyl | CONHCH₂(tetrahydrofuran-2-yl) |
| II-188 | 2,5-F₂-phenyl | CONHCH₂(tetrahydrofuran-2-yl) |
| II-189 | 4-F-phenyl | CONHCH₂(1-Et-pyrrolidin-2-yl) |
| II-190 | 4-OMe-phenyl | CONHCH₂(1-Et-pyrrolidin-2-yl) |
| II-191 | 5-F-phenyl | CONHCH₂(1-Et-pyrrolidin-2-yl) |
| II-192 | 5-OMe-phenyl | CONHCH₂(1-Et-pyrrolidin-2-yl) |
| II-193 | 3,6-(OMe)₂-phenyl | CONHCH₂(1-Et-pyrrolidin-2-yl) |
| II-194 | 4,5-F₂-phenyl | CONHCH₂(1-Et-pyrrolidin-2-yl) |
| II-195 | 5,6-F₂-phenyl | CONHCH₂(1-Et-pyrrolidin-2-yl) |
| II-196 | 3,6-F₂-phenyl | CONHCH₂(1-Et-pyrrolidin-2-yl) |
| II-197 | 4-F-phenyl | CO(morpholin-1-yl) |
| II-198 | 4-OMe-phenyl | CO(morpholin-1-yl) |
| II-199 | 5-F-phenyl | CO(morpholin-1-yl) |
| II-200 | 2,5-(OMe)₂-phenyl | CO(morpholin-1-yl) |
| II-201 | 4,5-F₂-phenyl | CO(morpholin-1-yl) |
| II-202 | 5,6-F₂-phenyl | CO(morpholin-1-yl) |
| II-203 | 2,5-F₂-phenyl | CO(morpholin-1-yl) |
| II-204 | 4-F-phenyl | CO(4-Me-piperidin-1-yl) |
| II-205 | 4-OMe-phenyl | CO(4-Me-piperidin-1-yl) |
| II-206 | 5-F-phenyl | CO(4-Me-piperidin-1-yl) |
| II-207 | 2,5-(OMe)₂-phenyl | CO(4-Me-piperidin-1-yl) |
| II-208 | 4,5-F₂-phenyl | CO(4-Me-piperidin-1-yl) |
| II-209 | 5,6-F₂-phenyl | CO(4-Me-piperidin-1-yl) |
| II-210 | 3,6-F₂-phenyl | CO(4-Me-piperidin-1-yl) |
| II-211 | 4-Cl-phenyl | CONHCH₂(pyrid-4-yl) |
| II-212 | 4,5-(OMe)₂-phenyl | CONHCH₂(pyrid-4-yl) |
| II-213 | 4-benzo[1,3]dioxo-5-yl | CONHCH₂(pyrid-4-yl) |
| II-214 | 4-Cl-phenyl | CONHCH₂(pyrid-3-yl) |
| II-215 | 4,5-(OMe)₂-phenyl | CONHCH₂(pyrid-3-yl) |
| II-216 | 4-benzo[1,3]dioxo-5-yl | CONHCH₂(pyrid-3-yl) |
| II-217 | 4-Cl-phenyl | CONHCH₂(tetrahydrofuran-2-yl) |
| II-218 | 4,5-(OMe)₂-phenyl | CONHCH₂(tetrahydrofuran-2-yl) |
| II-219 | 4-benzo[1,3]dioxo-5-yl | CONHCH₂(tetrahydrofuran-2-yl) |
| II-220 | 4-Cl-phenyl | CONHCH₂(1-Et-pyrrolidin-2-yl) |
| II-221 | 4,5-Cl₂-phenyl | CONHCH₂(1-Et-pyrrolidin-2-yl) |
| II-222 | 5-Cl-6-F-phenyl | CONHCH₂(1-Et-pyrrolidin-2-yl) |
| II-223 | 4-F-5-Cl-phenyl | CONHCH₂(1-Et-pyrrolidin-2-yl) |
| II-224 | 4,5-(OMe)₂-phenyl | CONHCH₂(1-Et-pyrrolidin-2-yl) |
| II-225 | 4-benzo[1,3]dioxo-5-yl | CONHCH₂(1-Et-pyrrolidin-2-yl) |

TABLE 1-continued

Compounds II

| No. | T—R² | Q—R⁴ |
|---|---|---|
| II-226 | 3,5-Cl₂-phenyl | CONHCH₂(1-Et-pyrrolidin-2-yl) |
| II-227 | 4-Cl-phenyl | CO(morpholin-1-yl) |
| II-228 | 4,5-(OMe)₂-phenyl | CO(morpholin-1-yl) |
| II-229 | 4-benzo[1,3]dioxo-5-yl | CO(morpholin-1-yl) |
| II-230 | 4-Cl-phenyl | CO(4-Me-piperidin-1-yl) |
| II-231 | 4,5-Cl₂-phenyl | CO(4-Me-piperidin-1-yl) |
| II-232 | 5-Cl-6-F-phenyl | CO(4-Me-piperidin-1-yl) |
| II-233 | 4-F-5-Cl-phenyl | CO(4-Me-piperidin-1-yl) |
| II-234 | 4,5-(OMe)₂-phenyl | CO(4-Me-piperidin-1-yl) |
| II-235 | 4-benzo[1,3]dioxo-5-yl | CO(4-Me-piperidin-1-yl) |
| II-236 | 3,5-Cl₂-phenyl | CO(4-Me-piperidin-1-yl) |
| II-237 | 5,6-F₂-phenyl | CON(Me)(Et) |
| II-238 | 4-F-phenyl | [N-Boc-3-(aminomethyl)piperidine amide] |
| II-239 | 5-OMe-phenyl | [N-Boc-3-(aminomethyl)piperidine amide] |
| II-240 | 2,5-(OMe)₂-phenyl | [N-Boc-3-(aminomethyl)piperidine amide] |
| II-241 | 4,5-F₂-phenyl | [N-Boc-3-(aminomethyl)piperidine amide] |
| II-242 | 5,6-F₂-phenyl | [N-Boc-3-(aminomethyl)piperidine amide] |

TABLE 1-continued
Compounds II
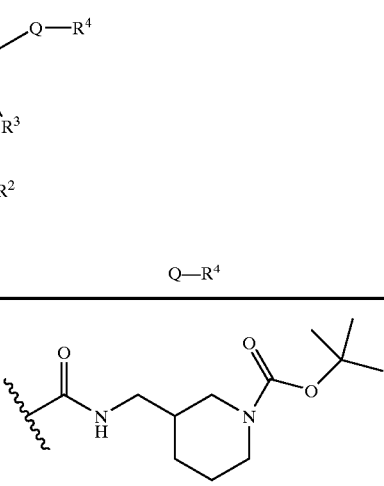
| No. | T—R² | Q—R⁴ |
|---|---|---|
| II-243 | 3,6-F₂-phenyl | 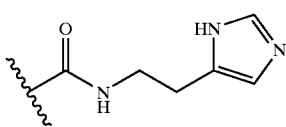 |
| II-244 | 5-MeO-phenyl | CONHOCH₂Ph |
| II-245 | 2,5-(OMe)₂-phenyl | CONHOCH₂Ph |
| II-246 | 5-F-phenyl | 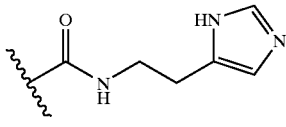 |
| II-247 | 5-MeO-phenyl | 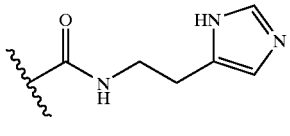 |
| II-248 | 4,5-F₂-phenyl | 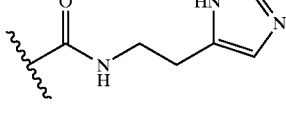 |
| II-249 | 5,6-F₂-phenyl | 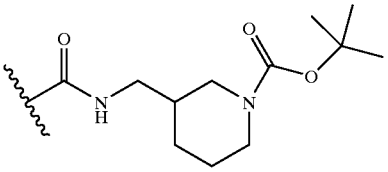 |
| II-250 | 5-Cl-phenyl | 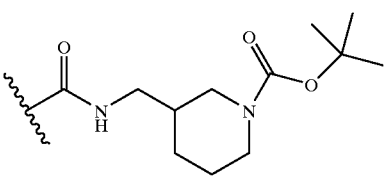 |
| II-251 | 4-Cl-phenyl |  |

TABLE 1-continued
Compounds II
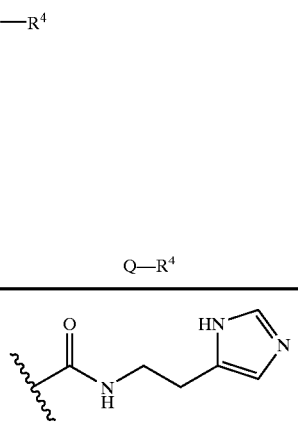
| No. | T—R² | Q—R⁴ |
|---|---|---|
| II-252 | 4-Cl-phenyl | 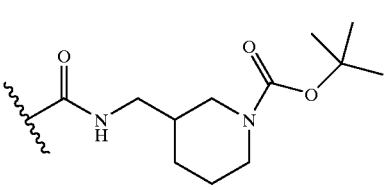 |
| II-253 | 4,5-Cl₂-phenyl | 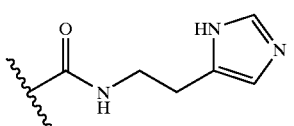 |
| II-254 | 4,5-Cl₂-phenyl | 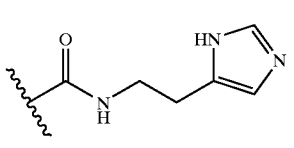 |
| II-255 | 2-F-3-Cl-phenyl | 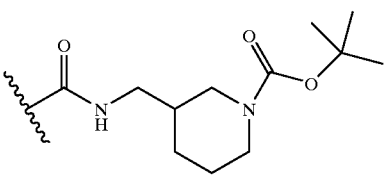 |
| II-256 | 4-F-5-Cl-phenyl | 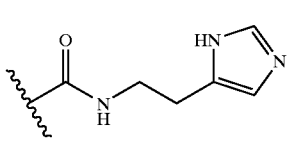 |
| II-257 | 4-F-5-Cl-phenyl | 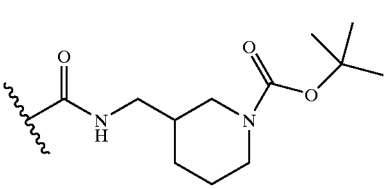 |
| II-258 | 4,5-(OMe)₂-phenyl | CON(Me)(Et) |
| II-259 | 4,5-(OMe)₂-phenyl |  |
| II-260 | 4,5-(OMe)₂-phenyl | CONHOCH₂Ph |

TABLE 1-continued

Compounds II

II

| No. | T—R² | Q—R⁴ |
|---|---|---|
| II-261 | 4,5-(OMe)₂-phenyl | [acyl-NH-CH₂CH₂-(1H-imidazol-4-yl)] |
| II-262 | 4-benzo[1,3]dioxo-5-yl | CON(Me)(Et) |
| II-263 | 4-benzo[1,3]dioxo-5-yl | [acyl-NH-CH₂-(1-Boc-piperidin-3-yl)] |
| II-264 | 4-benzo[1,3]dioxo-5-yl | CONHOCH₂Ph |
| II-265 | 4-benzo[1,3]dioxo-5-yl | [acyl-NH-CH₂CH₂-(1H-imidazol-4-yl)] |
| II-266 | 3,5-Cl₂-phenyl | [acyl-NH-CH₂CH₂-(1H-imidazol-4-yl)] |
| II-267 | 5-Br-phenyl | [acyl-(4-ethoxycarbonyl-piperidin-1-yl)] |
| II-268 | 5-Br-phenyl | [acyl-(4-(2-oxo-2,3-dihydro-1H-benzimidazol-1-yl)-piperidin-1-yl)] |
| II-269 | 5-Br-phenyl | [acyl-(4-(2-methylphenyl)-piperazin-1-yl)] |

TABLE 1-continued
Compounds II
II
| No. | T—R² | Q—R⁴ |
|---|---|---|
| II-270 | 5-Br-phenyl | 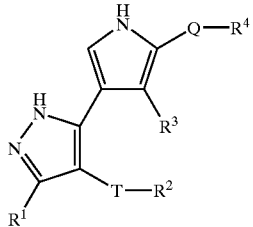 |
| II-271 | 5-Br-phenyl | 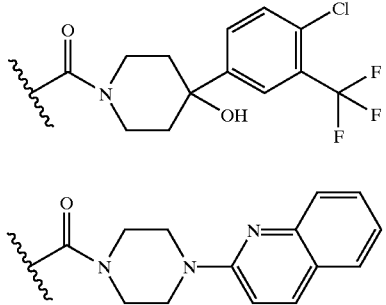 |
| II-272 | 5-Br-phenyl | 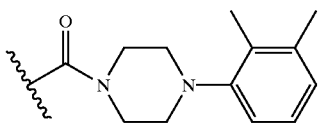 |
| II-273 | 5-Br-phenyl | 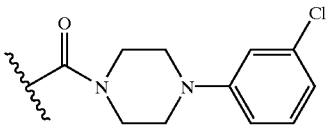 |
| II-274 | 5-Br-phenyl | 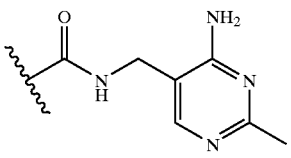 |
| II-275 | 5-Br-phenyl | 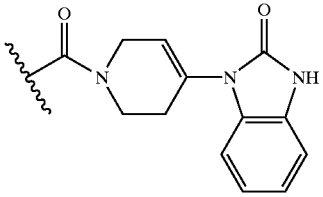 |
| II-276 | 5-Br-phenyl | 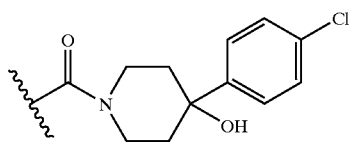 |

TABLE 1-continued
Compounds II
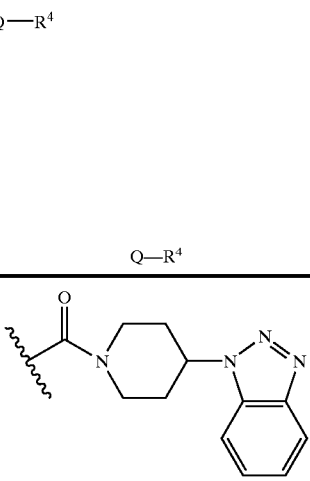
| No. | T—R² | Q—R⁴ |
|---|---|---|
| II-277 | 5-Br-phenyl | 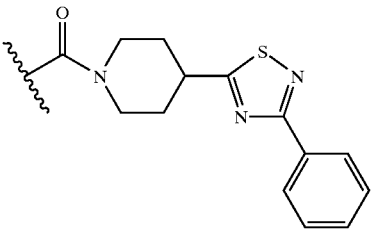 |
| II-278 | 5-Br-phenyl | 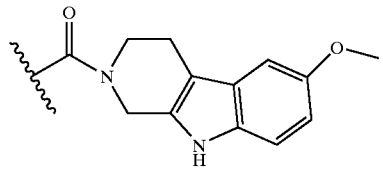 |
| II-279 | 5-Br-phenyl | 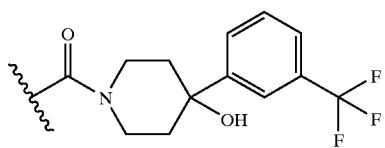 |
| II-280 | 5-Br-phenyl | CONH(CH₂)₂COOH |
| II-281 | 5-Br-phenyl | 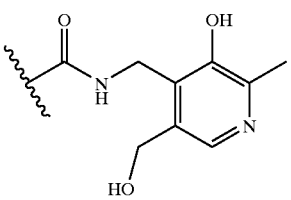 |
| II-282 | 5-Br-phenyl | CONHCH₂(4-COOH-phenyl) |
| II-283 | 5-Br-phenyl | 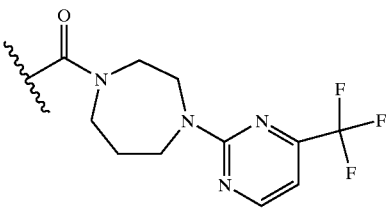 |
| II-284 | 5-Br-phenyl |  |

TABLE 1-continued

Compounds II

| No. | T—R² | Q—R⁴ |
|---|---|---|
| II-285 | 3-NO₂-phenyl | CONHCH₂phenyl |
| II-286 | 5-Cl-phenyl | CONHCH₂(1-Et-pyrrolidin-2-yl) |
| II-287 | 5-(N—Et—NHCO)-phenyl | CONHCH₂phenyl |
| II-288 | 5-Br-phenyl | *(structure: N-benzyl-N-(1-phenyl-2-hydroxyethyl) amide)* |
| II-289 | 5-NO₂-phenyl | CONHCH₂(pyrid-4-yl) |
| II-290 | 5-Br-phenyl | *(structure: N-(1-(2,3-dihydrobenzo[1,4]dioxin-6-yl)-2-phenoxyethyl) amide)* |
| II-291 | 5-F-phenyl | CON(Me)(Et) |
| II-292 | 5-MeO-phenyl | CON(Me)(Et) |
| II-293 | 5-Br-phenyl | *(structure: N-(1-(4-hydroxybenzyl)-2-hydroxyethyl) amide)* |
| II-294 | 5-Br-phenyl | *(structure: N-(1-(1H-imidazol-4-ylmethyl)-2-hydroxyethyl) amide)* |

TABLE 1-continued
Compounds II
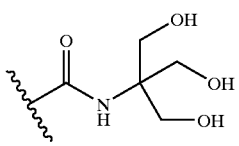
| No. | T—R² | Q—R⁴ |
|---|---|---|
| II-295 | 5-Br-phenyl | 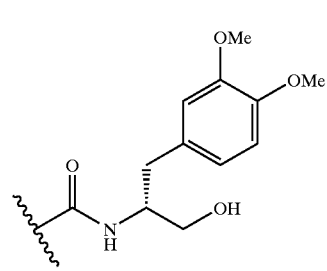 |
| II-296 | 5-Br-phenyl | 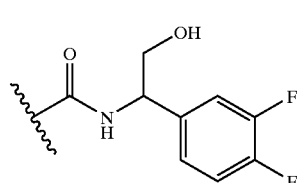 |
| II-297 | phenyl | $CONH(CH_2)_2NMe_2$ |
| II-298 | 5-MeO-phenyl | $CONH(CH_2)_2NMe_2$ |
| II-299 | 5-Br-phenyl | $CONHCH_2phenyl$ |
| II-300 | 3-Cl-phenyl | 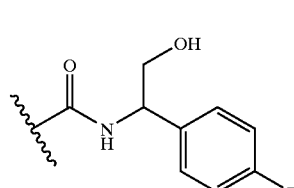 |
| II-301 | 3#Cl-phenyl | 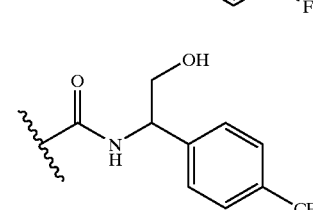 |
| II-302 | 3-Cl-phenyl | 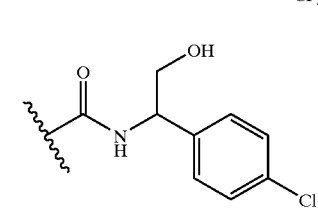 |
| II-303 | 3-Cl-phenyl |  |

TABLE 1-continued

Compounds II

| No. | T—R² | Q—R⁴ |
|---|---|---|
| II-304 | 3-Cl-phenyl | (S)-NH-CH(CH₂OH)-(3-Cl,4-F-phenyl) amide |
| II-305 | 3-Cl-phenyl | (R)-NH-CH(CH₂OH)-(3-Cl,4-F-phenyl) amide |
| II-306 | 3-Cl-phenyl | NH-CH(CH₂OH)-(3-F,4-OMe-phenyl) amide |
| II-307 | 3-Cl-phenyl | (S)-NH-CH(Ph)-CH₂-OC(O)CH₃ amide |
| II-308 | 3-Cl-phenyl | (S)-NH-CH(Ph)-CH₂-OC(O)OMe amide |
| II-309 | 3-Cl-phenyl | NH-CH(CH₂OH)-(3-OMe,4-F-phenyl) amide |

TABLE 1-continued
Compounds II
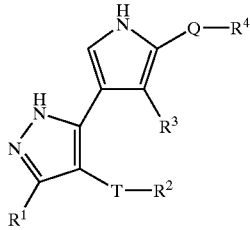
| No. | T—R² | Q—R⁴ |
|---|---|---|
| II-310 | 3,5-Cl₂-phenyl | 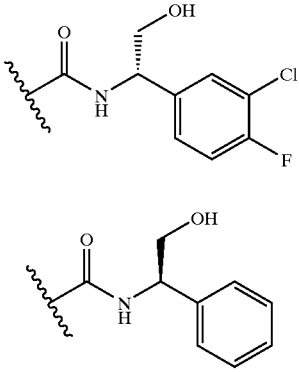 |
| II-311 | 3-Br-5-CF₃-phenyl | 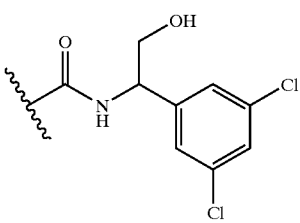 |
| II-312 | 3-Cl-phenyl | 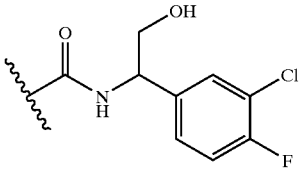 |
| II-313 | 3,5-Cl₂-phenyl | 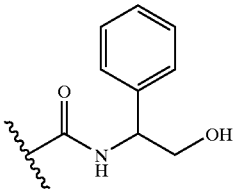 |
| II-314 | 3-Cl-4-CN-phenyl | 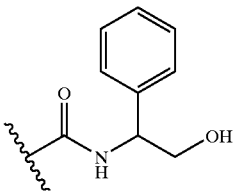 |
| II-315 | 3-Cl-4-CH₂OH-phenyl | |

TABLE 1-continued
Compounds II
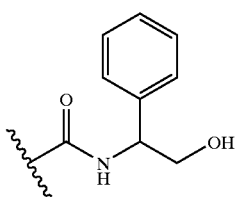
| No. | T—R² | Q—R⁴ |
|---|---|---|
| II-316 | 3-Cl-4-CH₂NH₂-phenyl | 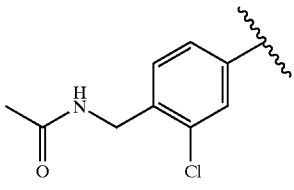 |
| II-317 | 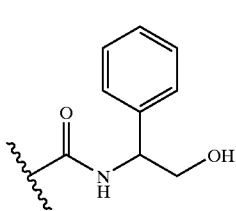 | 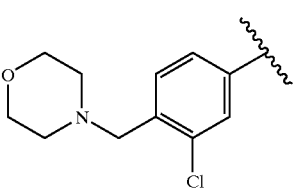 |
| II-318 | 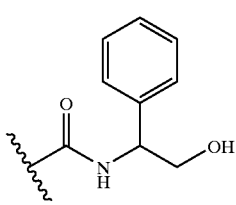 | 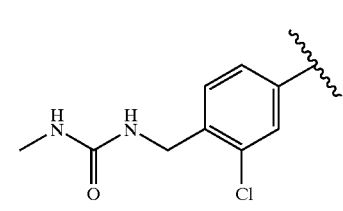 |
| II-319 | 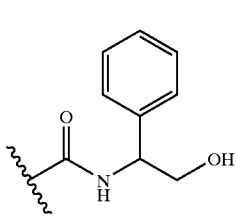 | 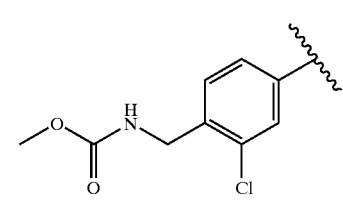 |
| II-320 | 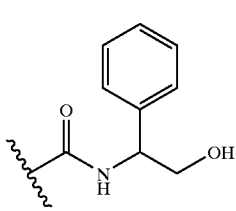 | 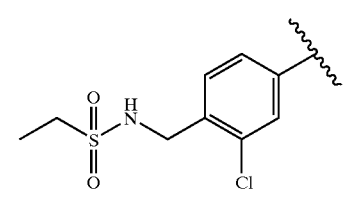 |
| II-321 | 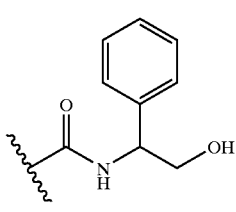 | |

TABLE 1-continued

Compounds II

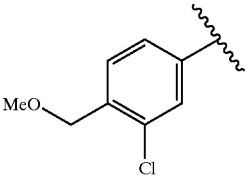

| No. | T—R² | Q—R⁴ |
|---|---|---|
| II-322 | 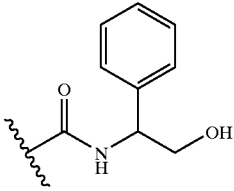 | 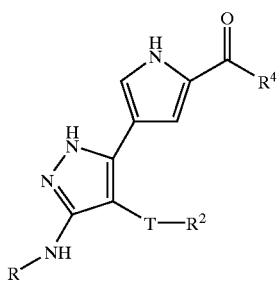 |
| II-323 | CH₂Ph | CON(Me)₂ |
| II-324 | cyclopentylmethyl | CO₂NHCH₂Ph |
| II-325 | isopropyl | CN |
| II-326 | 3-Cl-phenyl | NHCOCH₂Ph |
| II-327 | 3-Cl-phenyl | NHSO₂-morpholin-1-yl |
| II-328 | 3-Cl-phenyl | NHCONHCH₂Ph |
| II-329 | 3-Cl-phenyl | NHCO₂-tetrahydrofuran-2-yl |
| II-330 | CH₂Ph | CONHCH₂Ph |
| II-331 | Me | CONHCH₂Ph |
| II-332 | isopropyl | CONHCH₂Ph |
| II-333 | H | CON(Me)₂ |

Another preferred embodiment of this invention relates to compounds of formula II-B:

II-B wherein T, R, R², and R⁴ are as described above.

Preferred II-B compounds include those having one or more, and most preferably all, of the following features: (a) T is a valence bond; (b) R³ is hydrogen; and/or (c) R₂ is an optionally substituted aryl ring, more preferably an optionally substituted phenyl ring.

Exemplary structures of formula II-B, wherein R³ is H, are set out in Table 2 below.

TABLE 2

Compounds II-B

| No. | R | T-R² | Q-R⁴ |
|---|---|---|---|
| II-B-1 | H | phenyl | CON(Me)₂ |
| II-B-2 | H | phenyl | CO₂Et |
| II-B-3 | H | 3-NO₂-phenyl | CONHNH₂ |
| II-B-4 | H | phenyl | CO(pyrrolidin-1-yl) |
| II-B-5 | Me | phenyl | CONHCH₂(Ph) |
| II-B-6 | H | 3-NO₂-phenyl | CO₂Et |
| II-B-7 | H | 4-Cl-phenyl | CO₂Et |
| II-B-8 | Me | 4-OMe-phenyl | CO₂Et |
| II-B-9 | H | 3-NH₂-phenyl | CO₂Et |
| II-B-10 | H | 3-OMe-phenyl | CO₂Et |

TABLE 2-continued

Compounds II-B

| No. | R | T-R² | Q-R⁴ |
|---|---|---|---|
| II-B-11 | H | 4-F-phenyl | $CO_2Et$ |
| II-B-12 | H | 4-$NO_2$-phenyl | $CO_2Et$ |
| II-B-13 | Et | 3-Cl-phenyl | $CO_2Et$ |
| II-B-14 | H | 3-F-phenyl | $CO_2Et$ |
| II-B-15 | H | phenyl | $CO_2H$ |
| II-B-16 | Me | 3-Cl-phenyl | $CONHCH_2$(pyridin-4-yl) |
| II-B-17 | H | 5-Cl-phenyl | [structure: amide linked to 1-amino-2-hydroxyindane] |
| II-B-18 | H | 5-F-phenyl | $CONHCH_2$(tetrahydrofuran-2-yl) |
| II-B-19 | Me | 5,6-$F_2$-phenyl | CO(4-Me-piperidin-1-yl) |
| II-B-20 | H | 4-Cl-phenyl | $CONHCH_2$(pyrid-4-yl) |
| II-B-21 | H | 4,5-$(OMe)_2$-phenyl | [structure: amide linked to ethyl-imidazole (histamine)] |
| II-B-22 | Me | 4,5-$Cl_2$-phenyl | [structure: amide-CH₂-(N-Boc-piperidin-3-yl)] |
| II-B-23 | H | 3-Cl-phenyl | [structure: amide-CH(Ph)-CH₂-OAc] |
| II-B-24 | H | 3-Cl-phenyl | [structure: amide-CH(3,5-diCl-phenyl)-CH₂OH] |
| II-B-25 | Me | 3,5-$Cl_2$-phenyl | [structure: amide-CH(3-Cl-4-F-phenyl)-CH₂OH] |

TABLE 2-continued

Compounds II-B

| No. | R | T-R² | Q-R⁴ |
|---|---|---|---|
| II-B-26 | H | (ethylsulfonamido-chlorobenzyl group) | (phenyl-hydroxyethyl amide group) |
| II-B-27 | H | H | CON(Me)₂ |

The present compounds may be prepared in general by methods known to those skilled in the art for analogous compounds, as illustrated by the general Schemes I and II and the synthetic examples shown below.

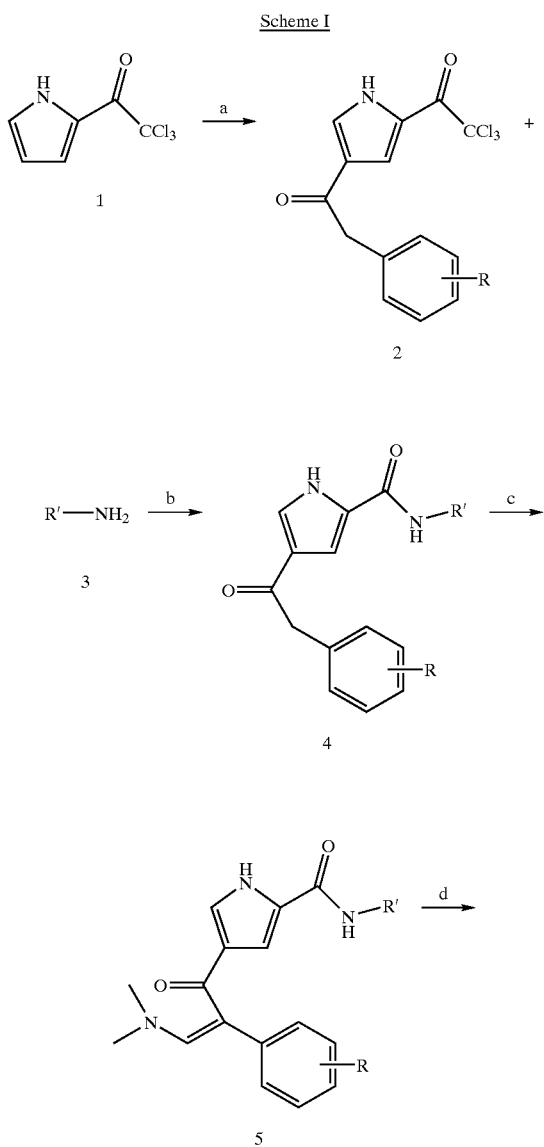

Scheme I

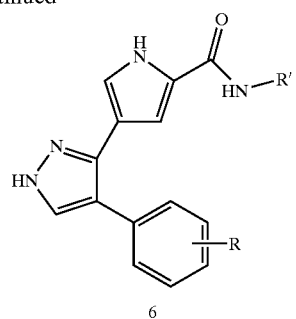

Reagents and conditions: (a) PhCH₂COCl, AlCl₃, CH₂Cl₂, 2 hours, RT (b) DMF, 24 hrs, room temperature (c) (Me₂N)₂-To-Bu, THF, 24 hrs, room temperature (d) H₂NNH₂, EtOH, 12 hours, reflux.

Scheme I above shows a general synthetic route that was used for preparing the compounds of this invention when R² is an optionally substituted phenyl group. In step (a), an optionally substituted benzoyl chloride was combined with compound 1 in dichloromethane and aluminum trichloride to form compound 2. A wide variety of substitutions on the phenyl ring are amenable to this reaction. Examples of suitable R² groups include, but are not limited to, those set forth in Table 1 above.

The formation of amide 4 was achieved by treating compound 2 with an amine 3 in DMF. When amine 3 was a primary amine, the reaction proceeded at ambient temperature. When amine 3 was a secondary amine, the reaction was heated at 50° C. to achieve complete reaction and afford amide 4.

The formation of enamine 5 at step (c) was achieved by treating amide 4 with (Me₂N)₂-To-Bu at ambient temperature. Alternatively, the reaction to form enamine 5 at step (c) was also achieved by using dimethylformamide-dimethylacetal (DMF-DMA). The reaction using DMF-DMA requires elevated temperature to afford enamine 5 whereas using (Me₂N)₂-OtBu has the advantage of proceeding at ambient temperature to afford the enamine 5 in higher purity.

The formation of the pyrazole compound 6 at step (d) was achieved by the treatment of enamine 5 with hydrazine hydrate at elevated temperature. The compounds of formula II synthesized by this method, as exemplified in Table 1, were isolated by preparatory HPLC (reverse phase, 10→90% MeCN in water over 15 minutes). The details of the conditions used for producing these compounds are set forth in the Examples.

Scheme II

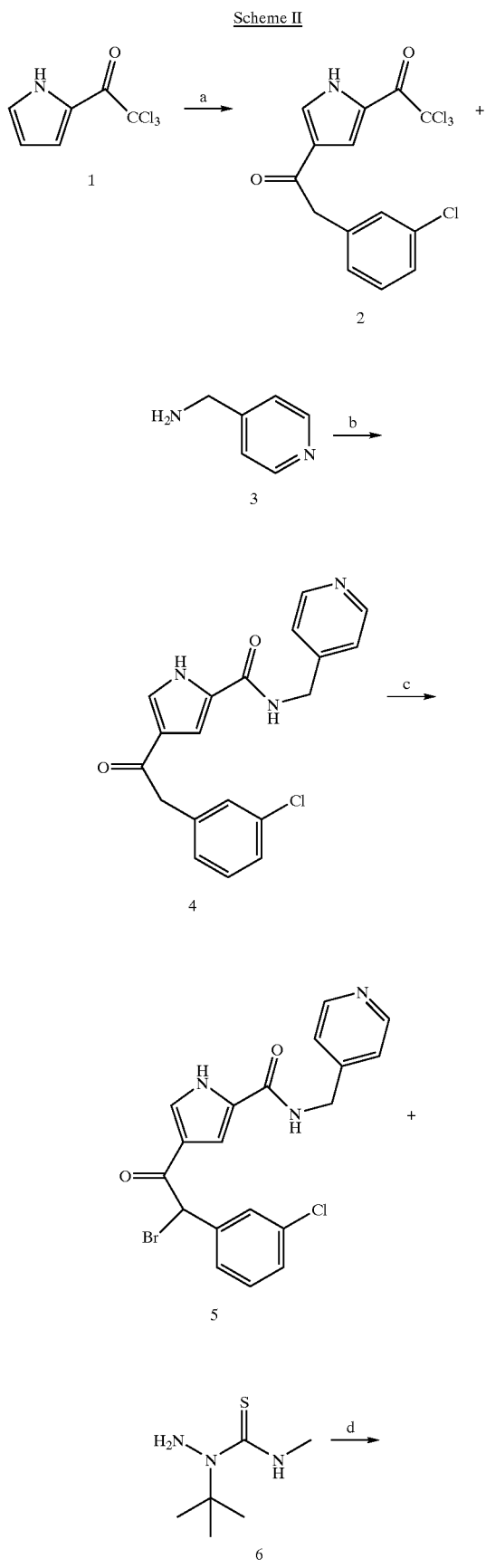

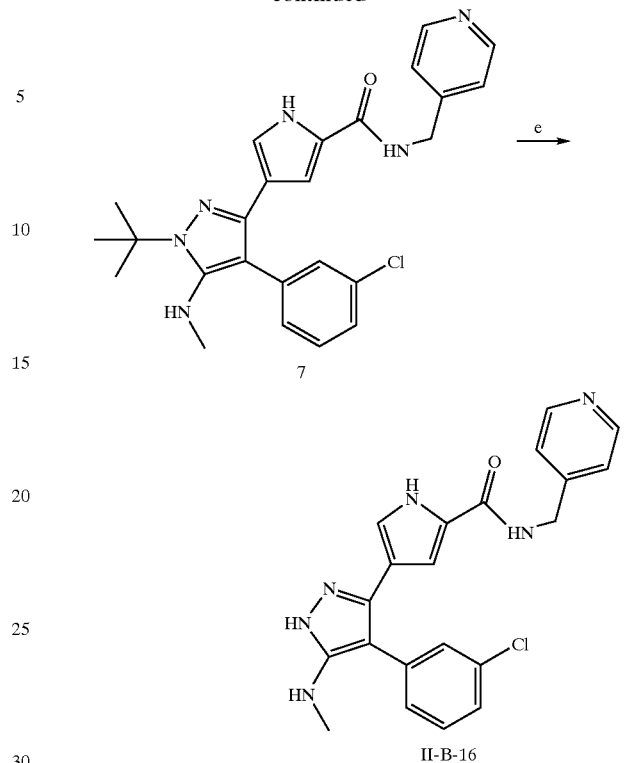

Reagents and conditions: (a) 3-Cl—PhCH$_2$COCl, AlCl$_3$, CH$_2$Cl$_2$, 2 hours, RT (b) DMF, 24 hrs, room temperature (c) NBS, CCl$_4$, reflux (d) iPrOH, reflux (e) formic acid, reflux, 2 hours.

Scheme II above shows a general synthetic method that may be used for preparing compounds of formula II-B, using compound II-B-16 as an example. This method is modified from that of Jira, T., et al, *Pharmazie*, pp. 401–406 (1994). Compounds of formula II-B may also be prepared by methods similar to those of Woller, J., et al, *Pharmazie*, pp. 937–940 (1996), Rychmans, T., et al, *Tetrahedron*, pp. 1729–1734 (1997), and Tupper, D. E., et al, *Synthesis*, pp. 337–341 (1997).

According to another embodiment, the invention provides a method of inhibiting kinase activity in a biological sample. This method comprises the step of contacting said biological sample with a compound of this invention.

The term "biological sample", as used herein includes cell cultures or extracts thereof; biopsied material obtained from a mammal or extracts thereof; and blood, saliva, urine, feces, semen, tears, or other body fluids or extracts thereof. The term "biological sample" also includes living organisms, in which case "contacting a compound of this invention with a biological sample" is synonymous with the term "administrating said compound (or composition comprising said compound) to a mammal."

Another aspect of this invention relates to a method for treating a disease state in mammals that is alleviated by treatment with a protein kinase inhibitor, which method comprises administering to a mammal in need of such a treatment a therapeutically effective amount of a compound having the formula

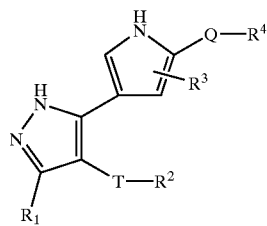

or a pharmaceutically acceptable derivative thereof, wherein:

$R^1$ is selected from R, halogen, $N(R^8)_2$, OR, NRCOR, NRCON$(R^8)_2$, CON$(R^8)_2$, SO$_2$R, NRSO$_2$R, or SO$_2$N$(R^8)_2$;

T is selected from a valence bond or a linker group;

each R is independently selected from hydrogen or an optionally substituted aliphatic group having one to six carbons;

$R^2$ is selected from hydrogen, CN, halogen, aryl, aralkyl, heteroaryl, heterocyclyl, an optionally substituted acyclic aliphatic chain group having one to six carbons, or an optionally substituted cyclic aliphatic group having four to ten carbons;

$R^3$ is selected from R, OH, OR, $N(R^8)_2$, halogen, or CN;

Q is a valence bond, J, or an optionally substituted $C_{1-6}$ alkylidene chain wherein up to two nonadjacent carbons of the alkylidene chain are each optionally and independently replaced by J;

J is selected from —C(=O)—, —CO$_2$—, —C(O)C(O)—, —NRCONR$^8$—, —N(R)N(R$^8$)—, —C(=O)NR$^8$—, —NRC(=O)—, —O—, —S—, —SO—, —SO$_2$—, —N(R)O—, —ON(R$^8$)—, —OC(=O)N(R$^8$)—, —N(R)COO—, —SO$_2$N(R$^8$)—, —N(R)SO$_2$—, or —N(R$^8$)—;

$R^4$ is selected from —R$^8$, —R$^5$, —NH$_2$, —NHR$^5$, —N(R$^5$)$_2$, or —NR$^5$ (CH$_2$)$_y$N(R$^5$)$_2$;

each $R^5$ is independently selected from $R^6$, $R^7$, —(CH$_2$)$_y$CH(R$^6$)(R$^7$), —(CH$_2$)$_y$R$^6$, —(CH$_2$)$_y$CH(R$^6$)$_2$, —(CH$_2$)$_y$CH(R$^7$)$_2$, or —(CH$_2$)$_y$R$^7$;

y is 0–6;

each $R^6$ is an optionally substituted group independently selected from an aliphatic, aryl, aralkyl, aralkoxy, heteroaryl, heteroarylalkyl, heteroarylalkoxy, heterocyclyl, heterocyclylalkyl, or heterocyclylalkoxy, group;

each $R^7$ is independently selected from an optionally substituted aliphatic, hydroxyalkyl, alkoxyalkyl, aryloxyalkyl, or alkoxycarbonyl;

and each $R^8$ is independently selected from R, or two $R^8$ on the same nitrogen taken together with the nitrogen optionally form a four to eight membered, saturated or unsaturated heterocyclic ring having one to three heteroatoms.

One embodiment comprises administering a compound of formula II. A preferred embodiment comprises administering a compound of formula II-A, and most preferably a compound listed in Table 1. Another preferred embodiment comprises administering a compound of formula II-B, and more preferably a compound listed in Table 2. Pharmaceutical compositions useful for such methods are described below.

The present method is especially useful for treating a disease state that is alleviated by the use of an inhibitor of ERK, JAK, JNK, Aurora, GSK, KDR, or AKT. As used herein, unless otherwise indicated, the terms "ERK", "JAK", "JNK", "Aurora", "GSK", "KDR", and "AKT" refer to all isoforms of the respective enzymes including, but not limited to, ERK1, ERK2, ERK3, ERK4, ERK5, ERK6, ERK7, JAK1, JAK2, JAK3, JAK4, JNK1, JNK2, JNK3, Auroral, Aurora2, GSK3-alpha, GSK3-beta, KDR, AKT-1, AKT-2, and AKT-3.

The activity of the compounds as protein kinase inhibitors, for example as ERK inhibitors, may be assayed in vitro, in vivo or in a cell line. Using ERK as an example, in vitro assays include assays that determine inhibition of either the kinase activity or ATPase activity of activated ERK. Alternate in vitro assays quantitate the ability of the inhibitor to bind to ERK and may be measured either by radiolabelling the inhibitor prior to binding, isolating the inhibitor/ERK complex and determining the amount of radiolabel bound, or by running a competition experiment where new inhibitors are incubated with ERK bound to known radioligands. one may use any type or isoform of ERK, depending upon which ERK type or isoform is to be inhibited.

The compounds of this invention are potent inhibitors of ERK as determined by enzymatic assay. These compounds have also been shown to inhibit ERK in a cell proliferation assay. The details of the conditions used for both the enzymatic and the cell proliferation assays are set forth in the Examples hereinbelow.

The compounds of this invention are also inhibitors of JNK, Aurora, GSK, KDR, and AKT as determined by enzymatic assay. The details of the conditions used for this assay are set forth in the Examples hereinbelow. Without being bound by theory, the compounds of this invention are also expected to inhibit other protein kinases.

The protein kinase inhibitors of this invention, or pharmaceutical salts thereof, may be formulated into pharmaceutical compositions for administration to animals or humans. These pharmaceutical compositions effective to treat or prevent a protein kinase-mediated condition which comprise the protein kinase inhibitor in an amount sufficient to detectably inhibit protein kinase activity and a pharmaceutically acceptable carrier, are another embodiment of the present invention. The term "detectably inhibit", as used herein means a measurable change in activity between a sample containing said inhibitor and a sample containing only a protein kinase.

The term "ERK-mediated condition", as used herein means any disease state or other deleterious condition in which ERK is known to play a role. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Compounds of the present invention are also useful as inhibitors of related kinases. The term "related kinases" refer to protein kinases having residues which are similar to those residues which line the ERK binding site. Without wishing to be bound by theory, applicants speculate that this inhibitory activity is due to the close structural similarity between the active sites of ERK and related kinases. The alignment of the ERK sequence with other kinases can be derived from common software programs such as the "bestfit" program available from Genetics Computer Group. This program uses the local homology algorithm described by Smith and Waterman in *Advances in Applied Mathematics* 2; 482 (1981).

Related kinases inhibited by the compounds of this invention would contain residues, identified by the above standard protein sequence alignment software, corresponding to the ERK residues: I31, E33, G34, A35, Y36, G37, M38, V39, A52, K54, R67, T68, E71, L75, I84, I86, I103, Q105, D106, L107, M108, E109, D111, K114, D149, K151, S153, N154, L156, C166, and D167, with a similarity score of 80% or greater. The similarity score may be determined using standard amino acid substitution tables such as those described by Dayhoff (Dayhoff, M. O., et al, *Atlas of Protein Sequence and Structure*, 1979) and Blosom-Henikoff (Blosum-Henikoff, S and Henikoff, J. G., *PNAS*, 1992, 89:10915–10919). The term "related kinases" also includes those containing residues with a similarity score of 80% or greater to the following ERK residues: I31, G37, A52, I103, E109, and N154.

Compounds of the present invention are also useful as inhibitors of JAK-family kinases. Without wishing to be bound by theory, applicants speculate that this inhibitory activity is due to the close structural similarity between the active sites of ERK and JAK as determined by the standard methods described above.

It has been found, from in-house x-ray crystal structure experiments with ERK-bound inhibitors, that three amino-acid residues in the ERK active site form key hydrogen bonding interactions with these types of inhibitors. These three amino-acid residues are M108, D106, and Q105. This amino acid numbering corresponds to the Swiss-Prot database entry for accession #P28482. The Swiss-Prot database is an international protein sequence database distributed by the European Bioinformatics Institute (EBI) in Geneva, Switzerland. The database can be found at www.ebi.ac.uk/swissprot.

The backbone atoms of M108 and D106, and the associated interactions, are common to all kinases. M108 provides both a hydrogen bond donor and acceptor and D106 provides a hydrogen bond acceptor through its backbone CO. An inhibitor that could form a hydrogen-bond to one or more of these hydrogen-bonding groups within the active site would be expected to bind to the enzyme and, therefore, show inhibition.

The Q105 glutamine residue is implicated in a subset of kinases that includes ERK and JAK as determined by examination of the alignment data obtained from the above mentioned software programs. Q105 provides a key hydrogen-bond accepting side-chain Co. Modeling experiments reveal that for both ERK and JAK, the hydrogen bond donor of the Ht-ring is within hydrogen-bonding distance to the Q105 residue. Because of these similar active-site interactions, the ERK inhibitors of the present invention inhibit JAK as well. Accordingly, these compounds are useful for treating JAK-mediated conditions.

The term "JAK-mediated condition", as used herein, means any disease state or other deleterious 15 condition in which JAK is known to play a role. Such conditions include, without limitation, allergic disorders such as asthma and atopic dermatitis, autoimmune diseases such as SLE lupus and psoriasis, and conditions associated with organ transplantations.

The compounds of this invention are also useful as inhibitors of JNK-family kinases. Accordingly, these compounds are useful for treating JNK-mediated conditions. The term "JNK-mediated condition", as used herein, means any disease state or other deleterious condition in which JNK is known to play a role. Such conditions include, without limitation, apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke, heart disease, immunodeficiency disorders, inflammatory diseases, allergic disorders, autoimmune diseases, destructive bone disorders such as osteoporosis, proliferative disorders, infectious diseases, viral diseases, disorders relating to cell death and hyperplasia including reperfusion/ischemia in stroke, heart attacks, and organ hypoxia, thrombin-induced platelet aggregation, chronic myelogenous leukemia (CML), rheumatoid arthritis, asthma, osteoarthritis, ischemia, cancer, liver disease including hepatic ischemia, heart disease such as myocardial infarction and congestive heart failure, pathologic immune conditions involving T cell activation and neurodegenerative disorders.

The compounds of this invention are also useful as inhibitors of Aurora. Accordingly, these compounds are useful for treating Aurora-mediated conditions. The term "Aurora-mediated condition", as used herein, means any disease or other deleterious condition in which Aurora is known to play a role. Such conditions include, without limitation, cancer. The term "cancer" includes, but is not limited to the following cancers: colon and ovarian.

The compounds of this invention are also useful as inhibitors of GSK family kinases. Accordingly, these compounds are useful for treating GSK-mediated conditions. The term "GSK-mediated condition", as used herein, means any disease state or other deleterious condition in which GSK is known to play a role. Such conditions include, without limitation, diabetes, Alzheimers disease, neurodegenerative diseases, and CNS disorders such as manic depressive disorder and schizophrenia.

The compounds of this invention are also useful as inhibitors of KDR family kinases. Accordingly, these compounds are useful for treating KDR-mediated conditions. The term "KDR-mediated condition", as used herein, means any disease state or other deleterious condition in which KDR is known to play a role. KDR-mediated diseases or conditions include, but are not limited to, cancer such as brain cancer, genitourinary tract cancer, lymphatic system cancer, stomach cancer, cancer of the larynx, lung cancer, pancreatic cancer, breast cancer, Kaposils sarcoma, and leukemia; endometriosis, benign prostatic hyperplasia; vascular diseases such as restenosis and atherosclerosis; autoimmune diseases such as rheumatoid arthritis and psoriasis; ocular conditions such as proliferative or angiogenic retinopathy and macular degeneration; and inflammatory diseases such as contact dermatitis, asthma and delayed hypersensitivity reactions.

The compounds of this invention are also useful as inhibitors of AKT family kinases. Accordingly, these compounds are useful for treating AKT-mediated conditions. The term "AKT-mediated condition", as used herein, means any disease state or other deleterious condition in which AKT is known to play a role. AKT-mediated diseases or conditions include, but are not limited to, proliferative disorders, cancer, and neurodegenerative disorders.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ $(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor of this invention that may be combined with the carrier materials to produce a single dosage form will vary depending upon the host treated, the particular mode of administration. Preferably, the compositions should be formulated so that a dosage of between about 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

The kinase inhibitors of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a kinase inhibitor of this invention are another embodiment of the present invention.

According to another embodiment, the invention provides methods for treating or preventing an ERK-, JAK-, JNK-, Aurora-, GSK-, KDR-, or AKT-mediated condition, or disease state, comprising the step of administering to a patient one of the above-described pharmaceutical compositions. The term "patient", as used herein, means a mammal, preferably a human.

Preferably, that method is used to treat or prevent a condition, or disease state, selected from cancers such as cancers of the breast, colon, prostate, skin, pancreas, brain, genitourinary tract, lymphatic system, stomach, larynx and lung, including lung adenocarcinoma and small cell lung cancer, stroke, diabetes, hepatomegaly, cardiomegaly, cardiovascular disease, Alzheimer's disease, cystic fibrosis, and viral disease, or any specific disease or disorder described above.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

In order that the invention described herein may be more fully understood, the following examples are set forth. It should be understood that these examples are for illustrative purposes only and are not to be construed as limiting this invention in any manner.

EXAMPLES

Example 1

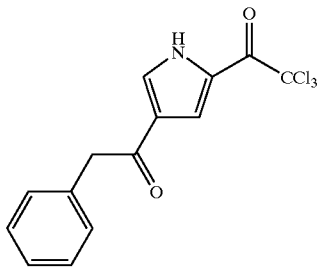

2,2,2-Trichloro-1-(4-phenylacetyl-1H-pyrrol-2-yl)-ethanone (1): In a dry flask, phenylacetyl chloride (1 equivalent) was combined with 2-trichloroacetyl pyrrole (1 equivalent) in a minimum amount of dichloromethane (DCM). To the resulting solution, at ambient temperature, was added aluminum trichloride (1 equivalent). After 2 hours, the reaction mixture was applied directly onto a silica gel column. Gradient elution with 10% ethyl acetate to 50% ethyl acetate in hexanes provided compound 1 in 60% yield. $^{1}$H NMR (CDCl$_{3}$) δ 4.0 (s, 2H), 7.1–7.35 (m, 7H), 9.7 (br s, NH). HPLC using method B (as described below for Example 5) provided retention time of 4.9 minutes. LC/MS (M+1) 330.2, (M−1) 328.1.

Example 2

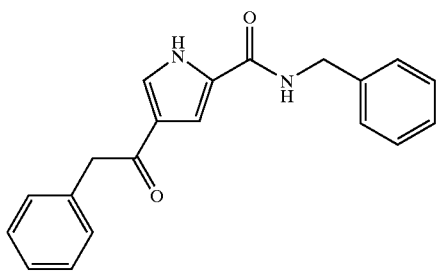

4-Phenylacetyl-1H-pyrrole-2-carboxylic acid benzylamide (2): To a solution of compound 1 (1 equivalent) in DMF, at ambient temperature, was added benzylamine (1.2 equivalents). After 24 hours, the solvent was evaporated and the crude product 2 was utilized without purification. HPLC using method B (as described below for Example 5) provided retention time of 3.8 minutes. FIA/MS (M+1) 319.3, (M−1) 317.2.

Example 3

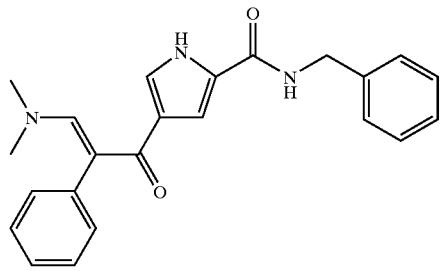

4-(3-Dimethylamino-2-phenyl-acryloyl)-1H-pyrrole-2-carboxylic acid benzylamide (3): To a solution of compound 2 (1 equivalent) in THF, at ambient temperature, was added (Me$_{2}$N)$_{2}$CHOt-Bu (3 equivalents). After 24 hours, the solvent was evaporated and the crude product 3 was utilized without purification. $^{1}$H NMR (CDCl$_{3}$) δ 4.4 (s, 2H), 4.8 (s, NH), 6.8–7.4 (m, 13H).

Example 4

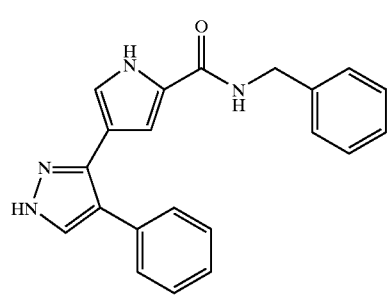

4-(4-phenyl-1H-pyrazole-3-yl)-1H-pyrrole-2-carboxylic acid benzylamide (II-5): To a solution of compound 3 (1 equivalent) in ethanol, at ambient temperature, was added hydrazine hydrate (3 equivalents) and the resulting mixture heated at reflux. After 12 hours, the solvent was evaporated and the crude product purified by preparatory HPLC (reverse phase; 10→90% MeCN in water; 15 minutes) to afford the desired compound II-5. LC/MS (M+1) 343.3, (M−1) 341.2.

Example 5

We have prepared other compounds of formula II by methods substantially similar to those described in the above Examples 1–4 and those illustrated in Scheme I. The characterization data for these compounds is summarized in Table 3 below and includes LC/MS, HPLC, and $^{1}$H NMR data.

For compounds where the HPLC Method is designated as "A", the following method was utilized: a gradient of water:MeCN, 0.1% TFA (95:5→0:100) was run over 22 minutes at 1 mL/min and 214 nm. For compounds where the HPLC Method is designated as "B", the following method was utilized: a gradient of water:MeCN, 0.1% TFA (90:10→0:100) was run over 8 minutes at 1 mL/min and 214 nm. Each of methods A and B utilize the YMC ODS-AQ 55 120A column with a size of 3.0×150 mm. The term "$T_{ret}$ (min)" refers to the retention time, in minutes, associated with the compound using the designated HPLC method.

Where applicable, $^1$H NMR data is also summarized in Table 3 below wherein "Y" designates $^1$H NMR data is available and was found to be consistant with structure. Compound numbers correspond to the compound numbers listed in Table 1.

TABLE 3

Characterization Data for Selected Compounds

| Compound No | M + 1 | M − 1 | HPLC Method | $T_{ret}$ (min) | $^1$H NMR |
|---|---|---|---|---|---|
| II-41 | 407.4 | 405.4 | A | 8.6 | Y |
| II-42 | 560.2 | 558.1 | A | 9.5 | — |
| II-43 | — | — | A | 10.5 | — |
| II-44 | 530.3 | 528.2 | A | 6.3 | — |
| II-45 | — | — | A | 9.8 | — |
| II-46 | — | — | A | 10.6 | — |
| II-50 | 377.4 | — | A | 10.1 | Y |
| II-52 | 530.2 | 528.2 | A | 10.3 | — |
| II-53 | 378.4 | 376.3 | A | 7.4 | Y |
| II-56 | 490.2 | 488.1 | A | 10.8 | — |
| II-58 | — | — | A | 10.46 | — |
| II-59 | — | — | A | 9.1 | — |
| II-63 | 361.4 | 359.3 | A | 9.5 | Y |
| II-65 | — | — | A | 10.0 | — |
| II-67 | 378.4 | 376.3 | A | 7.4 | Y |
| II-72 | 451.5 | 449.1 | A | 10.15 | Y |
| II-80 | 374.4 | 372.3 | A | 6.6 | — |
| II-83 | 435.3 | 433.4 | A | 10.3 | — |
| II-85 | — | — | A | 10.6 | — |
| II-86 | — | — | A | 9.3 | — |
| II-88 | 380.4 | 378.3 | A | 6.9 | — |
| II-89 | — | — | A | 10.5 | — |
| II-91 | — | — | A | 9.6 | — |
| II-92 | 377.4 | 375.3 | A | 10.2 | Y |
| II-94 | — | — | A | 9.0 | — |
| II-97 | 342.1 | — | B | 3.8 | Y |
| II-98 | 380.4 | 378.3 | A | 6.7 | — |
| II-102 | — | — | A | 10.3 | — |
| II-103 | — | — | A | 10.6 | — |
| II-105 | — | — | A | 9.3 | — |
| II-109 | — | — | A | 7.9 | — |
| II-110 | — | — | A | 10.3 | — |
| II-111 | 361.4 | 359.3 | A | 9.4 | Y |
| II-113 | — | — | A | 10.6 | — |
| II-116 | 380.2 | 378.4 | A | 6.9 | — |
| II-117 | 373.4 | — | A | 9.0 | Y |
| II-119 | 362.4 | 371.4 | A | 6.5 | — |
| II-120 | 373.4 | 371.4 | A | 8.2 | — |
| II-122 | — | — | A | 10.8 | — |
| II-123 | — | — | A | 11.4 | — |
| II-126 | — | — | A | 10.2 | — |
| II-128 | — | — | A | 10.9 | — |
| II-130 | — | — | A | 7.4 | — |
| II-133 | — | — | A | 9.5 | — |
| II-134 | 306.1 | — | B | 3.5 | Y |
| II-135 | 353.4 | 351.4 | A | 7.7 | — |
| II-137 | 313.3 | 311.2 | A | 6.4 | Y |
| II-141 | 380.4 | 378.3 | A | 6.7 | — |
| II-143 | 280.1 | — | B | 3.3 | Y |
| II-144 | 336.4 | — | B | 3.5 | — |
| II-145 | 373.4 | — | B | 2.8 | — |
| II-146 | — | — | A | 10.5 | — |
| II-147 | 362.4 | — | B | 3.5 | — |
| II-148 | 327.3 | 325.2 | A | 9.2 | Y |
| II-149 | 332.4 | — | B | 3.5 | — |
| II-150 | 322.4 | — | B | 3.2 | — |
| II-151 | 316.2 | 314.2 | A | 10.3 | Y |
| II-152 | — | — | A | 6.6 | — |
| II-153 | 323.4 | — | B | 2.3 | — |
| II-154 | 343.4 | — | B | 2.8 | — |
| II-158 | 294.3 | — | B | 3.4 | — |
| II-159 | 335.4 | — | B | 2.7 | — |
| II-161 | 389.3 | 387.2 | A | 8.9 | — |
| II-162 | 300.3 | 298.2 | A | 9.5 | Y |
| II-163 | 366.5 | 364.4 | B | 6.0 | — |
| II-164 | 297.3 | — | A | 5.1 | Y |
| II-165 | 322.3 | 325.2 | A | 9.7 | Y |

TABLE 3-continued

Characterization Data for Selected Compounds

| Compound No | M + 1 | M − 1 | HPLC Method | $T_{ret}$ (min) | $^1$H NMR |
|---|---|---|---|---|---|
| II-167 | 316.2 | 314.2 | A | 10.0 | Y |
| II-168 | 312.3 | 310.2 | A | 8.6 | Y |
| II-169 | 281.1 | — | B | 3.9 | Y |
| II-170 | 312.3 | 310.2 | A | 9.1 | Y |
| II-171 | 300.3 | 298.2 | A | 9.4 | Y |
| II-172 | 297.3 | 295.7 | A | 5.5 | Y |
| II-174 | 449.3 | 447.2 | A | 12.5 | Y |
| II-175 | 477.3 | 475.3 | A | 14.0 | Y |
| II-176 | 374.4 | 372.4 | A | 6.3 | — |
| II-178 | 362.4 | 360.0 | A | 6.6 | — |
| II-179 | 374.4 | 372.4 | A | 6.3 | — |
| II-180 | 404.4 | 402.4 | A | 6.4 | — |
| II-181 | 380.2 | 378.3 | A | 6.7 | — |
| II-182 | 355.4 | 353.4 | A | 7.7 | — |
| II-183 | 367.4 | 365.4 | A | 7.4 | — |
| II-184 | 355.4 | 353.4 | A | 7.9 | — |
| II-185 | 367.4 | 365.3 | A | 7.5 | — |
| II-186 | 397.4 | 395.4 | A | 7.1 | — |
| II-187 | 373.4 | 371.4 | A | 8.0 | — |
| II-188 | 373.4 | 371.4 | A | 7.9 | — |
| II-189 | 382.4 | 380.4 | A | 6.9 | — |
| II-190 | 394.4 | 392.4 | A | 6.7 | — |
| II-191 | 382.4 | 380.4 | A | 7.0 | — |
| II-192 | 394.5 | 392.4 | A | 6.7 | — |
| II-193 | 424.4 | 422.4 | A | 6.4 | — |
| II-194 | 400.4 | 398.4 | A | 7.3 | — |
| II-195 | 400.4 | 398.4 | A | 7.1 | — |
| II-196 | 400.4 | 398.4 | A | 7.2 | — |
| II-197 | 341.3 | 339.2 | A | 7.5 | — |
| II-198 | 353.4 | 351.4 | A | 7.1 | — |
| II-199 | 341.3 | 339.2 | A | 7.6 | — |
| II-200 | 383.4 | 381.4 | A | 6.9 | — |
| II-201 | 359.4 | 357.4 | A | 8.0 | — |
| II-202 | 359.4 | 357.4 | A | 7.8 | — |
| II-203 | 359.4 | 357.4 | A | 7.7 | — |
| II-204 | 354.4 | 352.4 | A | 6.2 | — |
| II-205 | 366.4 | 364.4 | A | 5.9 | — |
| II-206 | 354.4 | .52.4 | A | 5.6 | — |
| II-207 | 396.4 | 394.4 | A | 5.9 | — |
| II-208 | 372.4 | 370.4 | A | 6.7 | — |
| II-209 | 372.4 | 370.4 | A | 6.5 | — |
| II-210 | 372.4 | 370.4 | A | 6.4 | — |
| II-237 | — | — | A | 9.8 | — |
| II-238 | — | — | A | 11.6 | — |
| II-239 | — | — | A | 11.3 | — |
| II-240 | — | — | A | 7.5 | — |
| II-241 | — | — | A | 12.0 | — |
| II-242 | — | — | A | 11.7 | — |
| II-243 | — | — | A | 11.6 | — |
| II-244 | 389.4 | 387.3 | A | 10.2 | — |
| II-245 | — | — | A | 10.6 | — |
| II-246 | 365.4 | 363.4 | A | 7.5 | — |
| II-247 | — | — | A | 7.2 | — |
| II-248 | — | — | A | 8.0 | — |
| II-249 | — | — | A | 7.7 | — |
| II-267 | — | — | A | 10.7 | — |
| II-268 | — | — | A | 10.0 | — |
| II-269 | — | — | A | 12.2 | — |
| II-270 | — | — | A | 12.3 | — |
| II-271 | — | — | A | 9.3 | — |
| II-272 | — | — | A | 12.7 | — |
| II-273 | — | — | A | 12.7 | — |
| II-274 | — | — | A | 3.8 | — |
| II-275 | — | — | A | 10.3 | — |
| II-276 | — | — | A | 8.4 | — |
| II-277 | — | — | A | 10.6 | — |
| II-278 | — | — | A | 12.8 | — |
| II-279 | — | — | A | 11.4 | — |
| II-280 | — | — | A | 7.9 | — |
| II-281 | — | — | A | 11.5 | — |
| II-282 | — | — | A | 8.6 | — |
| II-283 | — | — | A | 8.4 | — |
| II-284 | — | — | A | 12.2 | — |
| II-290 | — | — | A | 11.4 | — |

TABLE 3-continued

Characterization Data for Selected Compounds

| Compound No | M + 1 | M − 1 | HPLC Method | T_ret (min) | ¹H NMR |
|---|---|---|---|---|---|
| II-291 | — | — | A | 9.7 | — |
| II-292 | — | — | A | 9.1 | — |
| II-293 | 481.3 | 479.3 | A | 8.3 | — |
| II-294 | 455.4 | 453.3 | A | 6.9 | — |
| II-295 | — | — | A | 7.5 | — |
| II-296 | — | — | A | 8.9 | — |
| II-298 | 353.4 | — | B | 2.8 | — |
| II-299 | 421.3 | 423.2 | A | 10.1 | — |

Example 6

ERK Inhibition Assay:

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $IC_{50}$ was evaluated from the rate data as a function of inhibitor concentration.

Table 4 shows the results of the activity of selected compounds of this invention in the ERK2 inhibition assay. The compound numbers correspond to the compound numbers in Table 1. Compounds having an activity designated as "A" provided a $K_i$ value below 1 micromolar; compounds having an activity designated as "B" provided a $K_i$ value between 1 and 5 micromolar; and compounds having an activity designated as "C" provided a $K_i$ value greater than 5 micromolar.

TABLE 4

ERK2 Inhibitory Activity of Selected Compounds

| No. | Activity | No. | Activity | No. | Activity |
|---|---|---|---|---|---|
| II-1 | A | II-2 | C | II-3 | A |
| II-4 | A | II-5 | A | II-6 | A |
| II-7 | C | II-8 | C | II-9 | C |
| II-10 | C | II-11 | C | II-12 | C |
| II-13 | A | II-14 | C | II-16 | C |
| II-17 | C | II-18 | A | II-19 | A |
| II-20 | A | II-21 | C | II-22 | A |
| II-23 | A | II-24 | A | II-25 | C |
| II-26 | A | II-27 | A | II-28 | A |
| II-29 | C | II-30 | A | II-31 | C |
| II-39 | A | II-40 | A | II-41 | A |
| II-42 | A | II-43 | A | II-44 | A |
| II-45 | A | II-46 | A | II-47 | A |
| II-48 | A | II-49 | A | II-50 | A |
| II-51 | A | II-52 | A | II-53 | A |
| II-54 | A | II-55 | A | II-56 | A |
| II-57 | A | II-58 | A | II-59 | A |
| II-60 | A | II-61 | A | II-62 | A |
| II-63 | A | II-64 | A | II-65 | A |
| II-66 | A | II-67 | A | II-68 | A |
| II-69 | A | II-70 | A | II-71 | A |
| II-72 | A | II-73 | A | II-74 | A |
| II-75 | A | II-76 | A | II-77 | A |
| II-78 | A | II-79 | A | II-80 | A |
| II-81 | A | II-82 | A | II-83 | A |

TABLE 4-continued

ERK2 Inhibitory Activity of Selected Compounds

| No. | Activity | No. | Activity | No. | Activity |
|---|---|---|---|---|---|
| II-84 | A | II-85 | A | II-86 | A |
| II-87 | A | II-88 | A | II-89 | A |
| II-90 | A | II-91 | A | II-92 | A |
| II-93 | A | II-94 | A | II-95 | A |
| II-96 | A | II-97 | A | II-98 | A |
| II-99 | A | II-100 | A | II-101 | A |
| II-102 | A | II-103 | A | II-104 | A |
| II-105 | A | II-106 | A | II-107 | A |
| II-108 | A | II-109 | A | II-110 | A |
| II-114 | A | II-115 | A | II-116 | B |
| II-117 | B | II-118 | B | II-119 | B |
| II-120 | B | II-121 | B | II-122 | B |
| II-123 | B | II-124 | B | II-125 | B |
| II-126 | B | II-127 | B | II-128 | B |
| II-129 | B | II-130 | B | II-131 | B |
| II-132 | B | II-133 | B | II-134 | B |
| II-135 | B | II-136 | B | II-137 | B |
| II-138 | B | II-139 | B | II-140 | B |
| II-141 | B | II-142 | B | II-143 | B |
| II-144 | B | II-145 | B | II-146 | B |
| II-147 | B | II-148 | B | II-149 | B |
| II-150 | B | II-151 | B | II-152 | B |
| II-153 | B | II-154 | B | II-155 | B |
| II-156 | B | II-157 | B | II-158 | B |
| II-159 | B | II-160 | B | II-161 | C |
| II-162 | C | II-163 | C | II-164 | C |
| II-165 | C | II-166 | C | II-167 | C |
| II-168 | C | II-169 | C | II-170 | C |
| II-171 | C | II-172 | C | II-285 | B |
| II-286 | C | II-287 | C | II-288 | B |
| II-289 | C | II-290 | B | II-291 | C |
| II-292 | C | II-293 | C | II-294 | C |
| II-295 | C | II-296 | C | II-297 | C |
| II-298 | C | II-299 | C | | |

Example 7

ERK Inhibition Cell Proliferation Assay:

Compounds were assayed for the inhibition of ERK2 by a cell proliferation assay. In this assay, a complete media was prepared by adding 10% fetal bovine serum and penicillin/streptomycin solution to RPMI 1640 medium (JRH Biosciences). Colon cancer cells (HT-29 cell line) were added to each of 84 wells of a 96 well plate at a seeding density of 10,000 cells/well/150 μL. The cells were allowed to attach to the plate by incubating at 37° C. for 2 hours. A solution of test compound was prepared in complete media by serial dilution to obtain the following concentrations: 20 μM, 6.7 μM, 2.2 μM, 0.74 μM, 0.25 μM, and 0.08 μM. The test compound solution (50 μL) was added to each of 72 cell-containing wells. To the 12 remaining cell-containing wells, only complete media (200 μL) was added to form a control group in order to measure maximal proliferation. To the remaining 12 empty wells, complete media was added to form a vehicle control group in order to measure background. The plates were incubated at 37° C. for 3 days. A stock solution of ³H-thymidine (1 mCi/mL, New England Nuclear, Boston, Mass.) was diluted to 20 μCi/mL in RPMI medium then 20 μL of this solution was added to each well. The plates were further incubated at 37° C. for 8 hours then harvested and analyzed for ³H-thymidine uptake using a liquid scintillation counter.

Selected compounds of this invention that inhibit ERK in the colon cell proliferation assay, with an $IC_{50}$ of less than 10 μM include: II-43, II-48, and II-45.

Example 8

JAK Inhibition Assay:

Compound inhibition of JAK may be assayed by the method described by G. R. Brown, et al, *Bioorg. Med. Chem. Lett.* 2000, vol. 10, pp 575–579 in the following manner. Into Maxisorb plates, previously coated at 4° C. with Poly (Glu, Ala, Tyr) 6:3:1 then washed with phosphate buffered saline 0.05% and Tween (PBST), is added 2 μM ATP, 5 mM $MgCl_2$, and a solution of compound in DMSO. The reaction is started with JAK enzyme and the plates incubated for 60 minutes at 30° C. The plates are then washed with PBST, 100 μL HRP—Conjugated 4G10 antibody is added, and the plate incubated for 90 minutes at 30° C. The plate is again washed with PBST, 100 μL TMB solution is added, then the plates are incubated for another 30 minutes at 30° C. Sulfuric acid (100 μL of 1M) is added to stop the reaction and the plate is read at 450 nM to obtain the optical densities for analysis to determine $IC_{50}$ values.

Example 9

JNK Inhibition Assay:

Compounds were screened in the following manner for their ability to inhibit JNK using a spectrophotometric coupled-enzyme assay. To an assay stock buffer solution containing 0.1 M HEPES buffer (pH 7.5), 10 mM $MgCl_2$, 2.5 mM phosphoenolpyruvate, 200 μM NADH, 150 μg/mL pyruvate kinase, 50 μg/mL lactate dehydrogenase, and 200 μM EGF receptor peptide (with sequence KRELVEPLTPSGEAPNQALLR), were added various concentrations of the compound in DMSO and a fixed concentration (10 nM) of activated JNK. The resulting mixture was incubated at 30° C. for 10 minutes then the reaction was initiated by the addition of 10 μM ATP. The decrease of absorbance at 340 nM at 30° C. was monitored as a function of time and the resulting data was fitted to a competitive inhibition kinetic model to determine the $K_i$.

Table 5 shows the results of the activity of selected compounds of this invention in the JNK inhibition assay. The compound numbers correspond to the compound numbers in Table 1. Compounds having an activity designated as "A" provided a $K_i$ value below 1 micromolar; compounds having an activity designated as "B" provided a $K_i$ value between 1 and 5 micromolar; and compounds having an activity designated as "C" provided a $K_i$ value greater than 5 micromolar.

TABLE 5

| JNK Inhibitory Activity of Selected Compounds | | | |
| --- | --- | --- | --- |
| No. | Activity | No. | Activity |
| II-39 | B | II-48 | A |
| II-40 | A | II-51 | B |
| II-43 | A | II-55 | A |
| II-46 | A | II-104 | B |
| II-47 | B | II-112 | C |

Example 10

Aurora Inhibition Assay:

Compounds were screened in the following manner for their ability to inhibit Aurora using a standard coupled enzyme assay. To an assay stock buffer solution containing 0.1M HEPES 7.5, 10 mM $MgCl_2$, 25 mM NaCl, 2.5 mM phosphoenolpyruvate, 300 μM NADH, 30 μg/mL pyruvate kinase, 10 μg/mL lactate dehydrogenase, 40 μM ATP, and 800 μM peptide (LRRASLG, American Peptide, Sunnyvale, Calif.) was added a 30 μM solution of the compound in DMSO and the resulting mixture incubated at 30° C. for 10 min. The reaction was initiated by the addition of 10 μL of 70 nM Aurora and 1 mM DTT. The rates of reaction were obtained by monitoring absorbance at 340 nM over a 5 minute read time at 30° C. using a BioRad Ultramark plate reader (Hercules, Calif.). The $IC_{50}$ was determined from the rate data as a function of inhibitor concentration.

Table 6 shows the results of the activity of selected compounds of this invention in the Aurora2 inhibition assay. The compound numbers correspond to the compound numbers in Table 1. Compounds having an activity designated as "A" provided an $IC_{50}$ value below 5 micromolar; compounds having an activity designated as "B" provided an $IC_{50}$ value between 5 and 10 micromolar; and compounds having an activity designated as "C" provided an $IC_{50}$ value greater than 10 micromolar.

TABLE 6

| Aurora2 Inhibitory Activity of Selected Compounds | | | | | |
| --- | --- | --- | --- | --- | --- |
| No. | Activity | No. | Activity | No. | Activity |
| II-48 | A | II-89 | A | II-211 | B |
| II-51 | B | II-93 | A | II-212 | B |
| II-54 | B | II-98 | B | II-213 | B |
| II-57 | A | II-99 | A | II-214 | B |
| II-61 | A | II-101 | A | II-215 | B |
| II-64 | A | II-103 | B | II-216 | B |
| II-66 | B | II-106 | B | II-218 | B |
| II-70 | B | II-108 | B | II-228 | A |
| II-72 | B | II-112 | A | II-252 | B |
| II-76 | A | II-113 | A | II-254 | A |
| II-77 | A | II-114 | A | II-255 | B |
| II-80 | C | II-115 | A | II-258 | C |
| II-81 | A | II-141 | A | II-259 | B |
| II-82 | A | II-142 | A | II-260 | C |
| II-85 | B | II-181 | B | II-262 | B |
| II-88 | B | II-188 | C | II-266 | B |

Example 11

GSK-3 Inhibition Assay:

Compounds were screened in the following manner for their ability to inhibit Glycogen Synthase Kinase 3 (GSK-3) using a standard coupled enzyme assay (Fox et al (1998) *Protein Sci* 7, 2249). To an assay stock buffer solution containing 0.1M HEPES 7.5, 10 mM $MgCl_2$, 25 mM NaCl, 2.5 mM phosphoenolpyruvate, 300 μM NADH, 1 mM DTT, 30 μg/mL pyruvate kinase, 10 μg/mL lactate dehydrogenase, 300 μM peptide (HSSPHQp-SEDEEE, American Peptide, Sunnyvale, Calif.), and 60 nM GSK-3, was added a 30 μM solution of the compound in DMSO and the resulting mixture incubated at 30° C. for 5 min. The reaction was initiated by the addition of 10 μM ATP. The rates of reaction were obtained by monitoring absorbance at 340 nM over a 5 minute read time at 30° C. using a Molecular Devices plate reader (Sunnyvale, Calif.). The $IC_{50}$ was determined from the rate data as a function of inhibitor concentration.

Table 7 shows the results of the activity of selected compounds of this invention in the GSK-3 inhibition assay. The compound numbers correspond to the compound numbers in Table 1. Compounds having an activity designated as "A" provided an $IC_{50}$ value below 10 micromolar; compounds having an activity designated as "B" provided an $IC_{50}$ value between 10 and 20 micromolar; and compounds having an activity designated as "C" provided an $IC_{50}$ value greater than 20 micromolar.

TABLE 7

GSK-3 Inhibitory Activity of Selected Compounds

| No. | Activity | No. | Activity | No. | Activity |
|---|---|---|---|---|---|
| II-89 | C | II-115 | C | II-263 | A |
| II-93 | C | II-127 | B | II-271 | A |
| II-94 | C | II-199 | C | II-278 | A |
| II-99 | A | II-214 | C | — | — |
| II-108 | B | II-227 | B | — | — |

Example 12

KDR Inhibition Assay:

Compounds were screened for their ability to inhibit KDR using a standard coupled enzyme assay (Fox et al., Protein Sci., (1998) 7, 2249). Assays were carried out in a mixture of 200 mM HEPES 7.5, 10 mM MgCl2, 25 mM NaCl, 1 mM DTT and 1.5% DMSO. Final substrate concentrations in the assay were 300 μM ATP (Sigma Chemicals) and 10 μM poly E4Y (Sigma). Assays were carried out at 37° C. and 30 nM KDR. Final concentrations of the components of the coupled enzyme system were 2.5 mM phosphoenolpyruvate, 200 μM NADH, 30 μg/ML pyruvate kinase and 10 μg/ml lactate dehydrogenase.

An assay stock buffer solution was prepared containing all of the reagents listed above, with the exception of ATP and the test compound of interest. 177 μl of the stock solution was placed in a 96 well plate followed by addition of 3 μl of 2 mM DMSO stock containing the test compound (final compound concentration 30 μM). The plate was preincubated for about 10 minutes at 37° C. and the reaction initiated by addition of 20 μl of ATP (final concentration 300 μM). Rates of reaction were obtained using a Molecular Devices plate reader (Sunnyvale, Calif.) over a 5 minute read time at 37° C. Compounds showing greater than 50% inhibition versus standard wells containing the assay mixture and DMSO without test compound were titrated to determine $IC_{50}$ values.

Selected compounds of this invention that inhibit KDR at 2 μM concentration in the above assay, with a percent inhibition of greater than 40%, include: II-43, II-48, II-304, and II-305.

Example 13

AKT Inhibition Assay:

Compounds were screened for their ability to inhibit AKT using a standard coupled enzyme assay (Fox et al., Protein Sci., (1998) 7, 2249). Assays were carried out in a mixture of 100 mM HEPES 7.5, 10 mM MgCl2, 25 mM NaCl, 1 mM DTT and 1.5% DMSO. Final substrate concentrations in the assay were 170 μM ATP (Sigma Chemicals) and 200 μM peptide (RPRAATF, American Peptide, Sunnyvale, Calif.). Assays were carried out at 30° C. and 45 nM AKT. Final concentrations of the components of the coupled enzyme system were 2.5 mM phosphoenolpyruvate, 300 μM NADH, 30 μg/ML pyruvate kinase and 10 μg/ml lactate dehydrogenase.

An assay stock buffer solution was prepared containing all of the reagents listed above, with the exception of AKT, DTT, and the test compound of interest. 56 μl of the stock solution was placed in a 384 well plate followed by addition of 1 μl of 2 mM DMSO stock containing the test compound (final compound concentration 30 μM). The plate was pre-incubated for about 10 minutes at 30° C. and the reaction initiated by addition of 10 μl of enzyme (final concentration 45 nM) and 1 mM DTT. Rates of reaction were obtained using a BioRad Ultramark plate reader (Hercules, Calif.) over a 5 minute read time at 30° C. Compounds showing greater than 50% inhibition versus standard wells containing the assay mixture and DMSO without test compound were titrated to determine $IC_{50}$ values.

Selected compounds of this invention that inhibit AKT include: II-89, II-94, and II-305.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:

1. A compound of formula I:

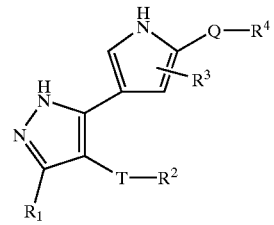

or a pharmaceutically acceptable derivative or prodrug thereof, wherein;

$R^1$ is selected from R, halogen, $N(R^8)_2$, OR, NRCOR, $NRCON(R^8)_2$, $CON(R^8)_2$, $SO_2R$, $NRSO_2R$, or $SO_2N(R^8)_2$;

T is selected from a valtence bond or a linker group selected from:

—O—, —S—, —NH₂—, or an optionally substituted $C_{1-6}$ alkylidene chain wherein up to two saturated carbons of the chain are optionally replaced by —C(=O)—, —CONH—, CONHNH—, —CO₂—, —NHCO₂—, —O—, —NHCONH—, —OC(=O)—, —OC(=O)NH—, —NHNH—, —NHCO—, —O—, —S—, —SO—, —SO₂—, —NH—, —SO₂NH—, or NHSO₂—;

each R is independently selected from hydrogen or an optionally substituted aliphatic group having one to six carbons;

$R^2$ is selected from hydrogen, CN, halogen, aryl, aralkyl, heteroaryl, heterocyclyl, an optionally substituted acyclic aliphatic chain group having one to six carbons, or an optionally substituted cyclic aliphatic group having four to ten carbons;

$R^3$ is selected from R, OH, OR, $N(R^8)_2$, halogen, or CN;

Q is J;

J is —C(=O)—;

$R^4$ is —NHR⁵;

$R^5$ —(CH₂)$_y$CH(R⁶) (R⁷);

y is 0–6;

$R^6$ is an optionally substituted group selected from an aryl, aralkyl, aralkoxy, heteroaryl, heteroarylalkyl, heteroarylalkoxy, heterocyclyl, heterocyclylalkyl, or heterocyclylalkoxy, group;

$R^7$ is independently selected from an optionally substituted aliphatic, hydroxyalkyl, alkoxyalkyl, aryloxyalkyl, or alkoxycarbonyl;

each $R^8$ is independently selected from R, or two $R^8$ on the same nitrogen taken together with the nitrogen optionally form a four to eight membered, saturated or unsaturated heterocyclic ring having one to three heteroatoms;

and each substitutable ring nitrogen is optionally substituted by R, NR₂, COR, CO₂($C_1$–$C_6$ optionally substituted alkyl), SO₂ ($C_1$–$C_6$ optionally substituted alkyl), CONR₂, and SO₂NR₂.

2. The compound according to claim 1 having the formula

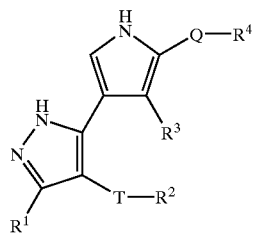

II or a pharmaceutically acceptable derivative or prodrug thereof.

3. The compound according to claim 2 having one or more of the following features: (a) T is a valence bond; (b) $R^1$ is hydrogen or NHR; (c) $R^2$ is an optionally substituted aryl ring; and (d) $R^3$ is hydrogen.

4. The compound according to claim 1 wherein said compound is selected from the following Table 1 compounds:

TABLE 1

Compounds II

| No. | T-R² | Q-R⁴ |
|---|---|---|
| II-39 | 3,5-Cl₂-phenyl | [structure: CONH-CH(Ph)-CH₂OH] |
| II-41 | 5-Cl-phenyl | CONH(2-OH-1-Ph-ethyl) |
| II-42 | 4-OH,3-I,5-nitrophenyl | CONH(2-OH-1-Ph-ethyl) |
| II-44 | 3-NH₂, 4-OH, 5-I-phenyl | CONH(2-OH-1-Ph-ethyl) |
| II-49 | 5-CF₃-phenyl | CONH(2-OH-1-Ph-ethyl) |
| II-59 | 5-Br-phenyl | [structure: CONH-CH(Ph)-CH₂CH₂OH] |
| II-62 | 5-Br-phenyl | CONH(1-Ph-propyl) |
| II-72 | 5-Br-phenyl | CONH(2-OH-1-Ph-ethyl) |
| II-75 | 5-Me-phenyl | CONH(2-OH-1-Ph-ethyl) |
| II-86 | 5-Br-phenyl | CONH(3-OH-1-Ph-propyl) |
| II-91 | 5-Br-phenyl | [structure: CONH-CH(CH₂Ph)-CH₂OH] |

TABLE 1-continued
Compounds II
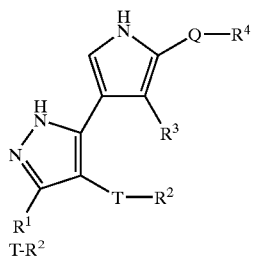
| No. | T-R² | Q-R⁴ |
|---|---|---|
| II-174 | 5-Cl-phenyl | 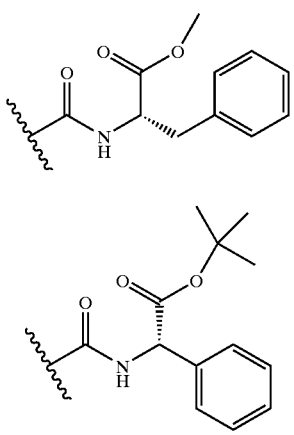 |
| II-175 | 5-Cl-phenyl | 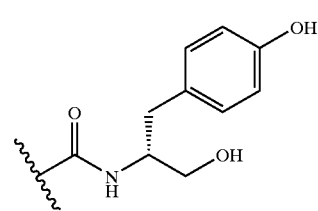 |
| II-293 | 5-Br-phenyl | 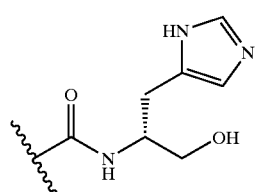 |
| II-294 | 5-Br-phenyl | 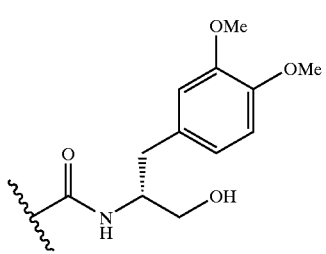 |
| II-296 | 5-Br-phenyl | 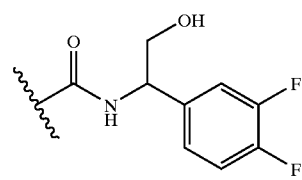 |
| II-300 | 3-Cl-phenyl | |

TABLE 1-continued
Compounds II
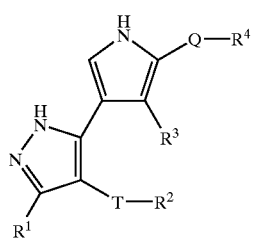
II
| No. | T-R² | Q-R⁴ |
|---|---|---|
| II-301 | 3-Cl-phenyl | 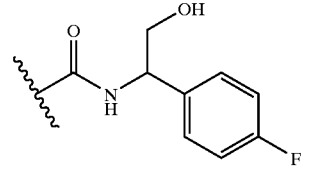 |
| II-302 | 3-Cl-phenyl | 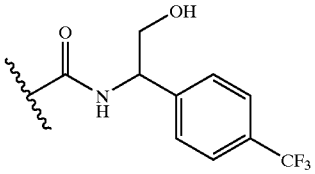 |
| II-303 | 3-Cl-phenyl | 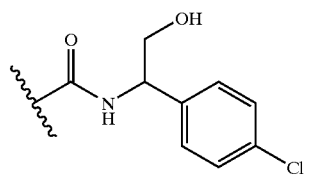 |
| II-304 | 3-Cl-phenyl | 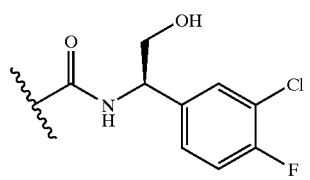 |
| II-305 | 3-Cl-phenyl | 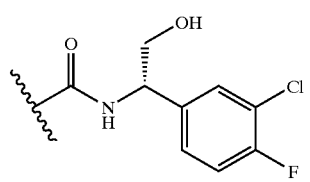 |
| II-306 | 3-Cl-phenyl | 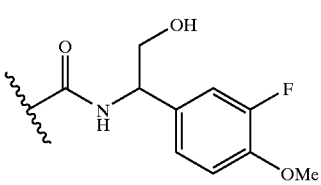 |

TABLE 1-continued
Compounds II
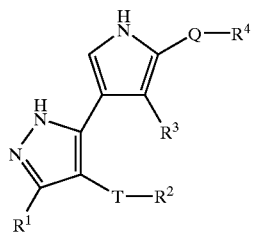
| No. | T-R² | Q-R⁴ |
|---|---|---|
| II-307 | 3-Cl-phenyl | 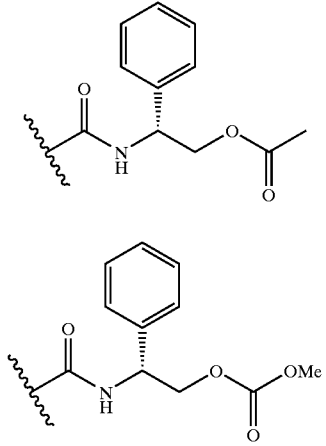 |
| II-308 | 3-Cl-phenyl | 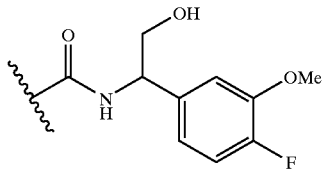 |
| II-309 | 3-Cl-phenyl | 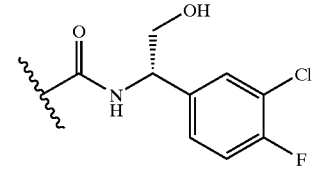 |
| II-310 | 3,5-Cl₂-phenyl | 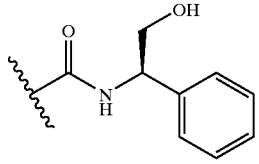 |
| II-311 | 3-Br-5-CF₃-phenyl | 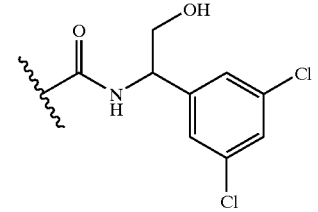 |
| II-312 | 3-Cl-phenyl |  |

TABLE 1-continued
Compounds II
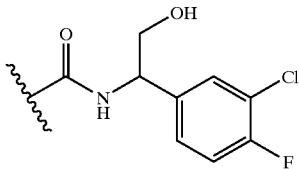
| No. | T-R² | Q-R⁴ |
|---|---|---|
| II-313 | 3,5-Cl₂-phenyl | 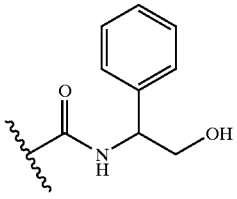 |
| II-314 | 3-Cl-4-CN-phenyl | 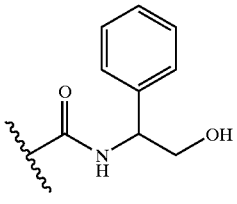 |
| II-315 | 3-Cl-4-CH₂OH-phenyl | 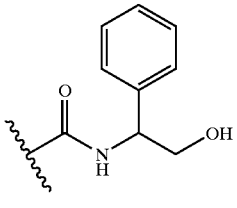 |
| II-316 | 3-Cl-4-CH₂NH₂-phenyl | 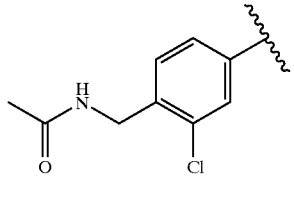 |
| II-317 | 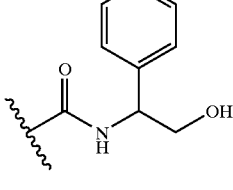 | 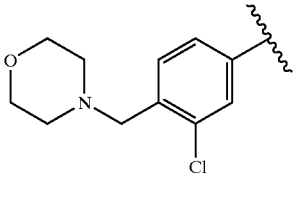 |
| II-318 | 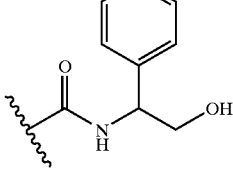 | |

TABLE 1-continued

Compounds II

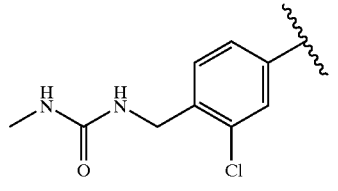

| No. | T-R² | Q-R⁴ |
|---|---|---|
| II-319 | 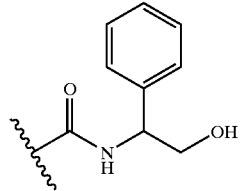 | 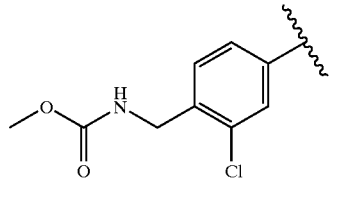 |
| II-320 | 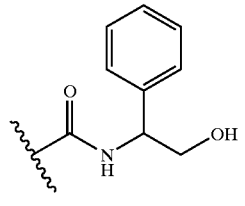 | 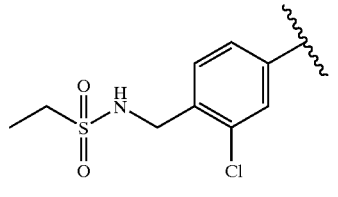 |
| II-321 | 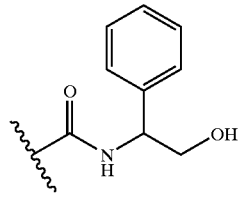 |  |
| II-322 | 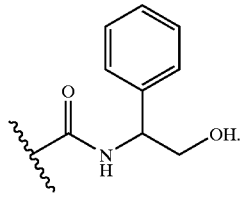 | 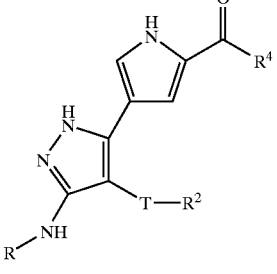 |

5. The compound according to claim 1 having the formula:

II-B

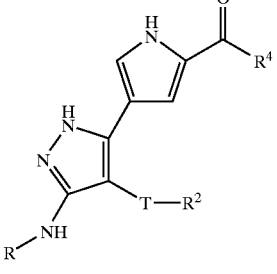

or a pharmaceutically acceptable derivative or prodrug thereof.

6. The compound according to claim 5 wherein:

T is a valence bond; and

R² is an optionally substituted aryl ring.

7. The compound according to claim 1 wherein said compound is selected from the following Table 2 compounds:

TABLE 2

Compounds II-B

II-B

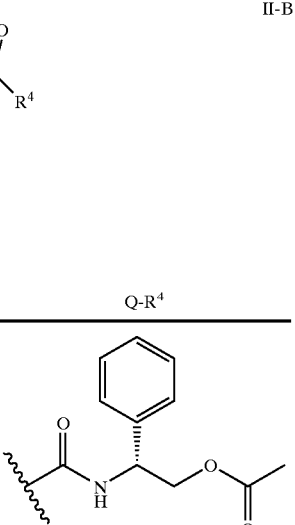

| No. | R | T-R² | Q-R⁴ |
|---|---|---|---|
| II-B-23 | H | 3-Cl-phenyl | 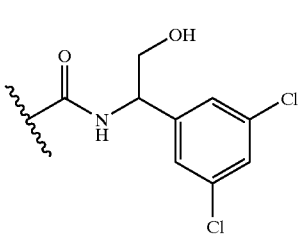 |
| II-B-24 | H | 3-Cl-phenyl | 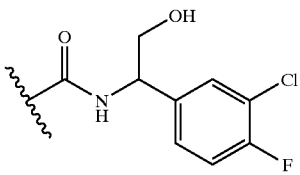 |
| II-B-25 | Me | 3,5-Cl₂-phenyl | |
| II-B-26 | H | | 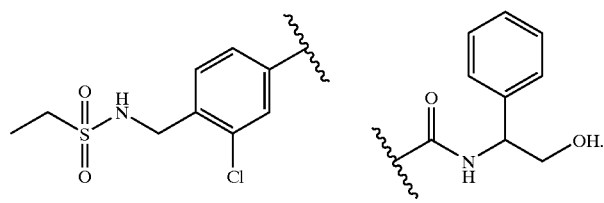 |

8. A composition comprising a compound according to any one of claims 1–3 or 6–9 in an amount sufficient to detectably inhibit protein kineseh activity, said protein kinase selected from one or more of ERK, JAK, JNK, Aurora, GSK, KDR, ART, or a protein kinase related thereto; and a pharmaceutically acceptable carrier.

9. The composition according to claim 8 wherein said compound is formulated in a pharmaceutically acceptable manner for administration to a patient.

10. A composition according to claim 8 further comprising a therapeutic agent, either as part of a multiple dosage form together with said compound or as a separate dosage form.

11. A method of inhibiting protein kinase activity in a biological sample, wherein said protein kinase is selected from ELK, JAK, JNK, Aurora, GSK, KDR, AKT, or a protein kinase related thereto, comprising the step of contacting said sample with a compound according to any one of claims 1–3 or 6–9.

12. A method for treating a protein kinase-mediated disease state in a patient, wherein said protein kinase is selected from one or more of ERK, JAK, JNK, Aurora, KDR, AKT, or a protein kinase related thereto, comprising the step of administering to said patient a composition according to claim 11.

13. The method according to claim 12, comprising the additional step of administering to said patient a therapeutic agent either as part of a multiple dosage form together with said compound or as a separate dosage form.

14. A method of treating a disease state in a patient, wherein said disease state is selected from cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, or CNS disorders, comprising the step of administering to said patient a composition according to claim 10.

15. The method according to claim 14 wherein the disease state is cancer.

16. The method according to claim 15 wherein the disease state is a cancer selected from breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; or leukemnia.

17. The method according to claim 15 comprising the additional step of administering to said patient a chemotherapeutic agent either as part of a multiple dosage form together with said compound or as a separate dosage form.

18. The method according to claim 14 wherein the disease state is cardiovascular disease.

19. The method according to claim 18 wherein the disease state is a cardiovascular disease selected from restenosis, cardiomegaly, artherosclerosis, myocardial infarction, or congestive heart failure.

20. The method according to of claim 18 comprising the additional step of administering to said patient a therapeutic agent for treating cardiovascular disease either as part of a multiple dosage form together with said compound or as a separate dosage form.

21. A composition for coating an implantable device comprising a compound according to claim 1 and a carrier suitable for coating said implantable device.

\* \* \* \* \*

UNITED STATES PATENT AND TRADEMARK OFFICE
CERTIFICATE OF CORRECTION

PATENT NO.      : 6,528,509 B1
DATED           : March 4, 2003
INVENTOR(S)     : Michael Hale et al.

It is certified that error appears in the above-identified patent and that said Letters Patent is hereby corrected as shown below:

<u>Title page,</u>
Item [75], Inventors, please delete the following inventors:
"Xiaoling Xie, Jeremy Green, Jingrong Cao, Christopher Baker, Michael Mullican, and Robert Marshal".

Signed and Sealed this

Second Day of March, 2004

JON W. DUDAS
*Acting Director of the United States Patent and Trademark Office*